United States Patent
Goto et al.

(10) Patent No.: US 8,304,961 B2
(45) Date of Patent: Nov. 6, 2012

(54) METHOD FOR TESTING PIEZOELECTRIC/ELECTROSTRICTIVE DEVICE, TESTING APPARATUS, AND METHOD FOR ADJUSTING PIEZOELECTRIC/ELECTROSTRICTIVE DEVICE

(75) Inventors: Naoki Goto, Nagoya (JP); Takao Ohnishi, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 12/905,296

(22) Filed: Oct. 15, 2010

(65) Prior Publication Data

US 2011/0025171 A1   Feb. 3, 2011

Related U.S. Application Data

(63) Continuation of application No. PCT/JP2009/057797, filed on Apr. 17, 2009.

(30) Foreign Application Priority Data

Apr. 18, 2008  (JP) .................................. 2008-109567
Dec. 25, 2008  (JP) .................................. 2008-330491

(51) Int. Cl.
  *H01L 41/107* (2006.01)
  *G01H 1/00* (2006.01)
  *G01R 29/22* (2006.01)
  *C23C 14/54* (2006.01)

(52) U.S. Cl. ............. 310/318; 73/570; 324/727; 427/10
(58) Field of Classification Search .................... 73/579; 324/727; 427/10; 310/318
See application file for complete search history.

(56) References Cited

U.S. PATENT DOCUMENTS

| | | | | |
|---|---|---|---|---|
| 6,222,302 | B1 | 4/2001 | Imada et al. | |
| 6,638,269 | B2 * | 10/2003 | Wilcox | 604/528 |
| 6,819,028 | B2 * | 11/2004 | Takatsuka et al. | 310/318 |
| 2002/0020218 | A1 | 2/2002 | Ishitoko et al. | |
| 2005/0284224 | A1 * | 12/2005 | Yamada et al. | 73/579 |
| 2007/0159028 | A1 | 7/2007 | Nagaya et al. | |
| 2009/0139087 | A1 * | 6/2009 | Hirota | 29/890.1 |

FOREIGN PATENT DOCUMENTS

| | | | |
|---|---|---|---|
| CN | 101968520 A | * | 8/2010 |
| JP | 07-305724 A | * | 11/1995 |
| JP | 11-168246 A1 | | 6/1999 |
| JP | 2002-005664 A1 | | 1/2002 |
| JP | 2006-108639 A1 | | 4/2006 |
| JP | 2008-245339 | * | 3/2007 |
| JP | 2010-050382 A | * | 3/2010 |
| JP | 2010-082939 A | * | 4/2010 |
| WO | 2005/104258 A1 | | 11/2005 |

* cited by examiner

*Primary Examiner* — Thomas Dougherty
(74) *Attorney, Agent, or Firm* — Burr & Brown

(57) ABSTRACT

There is provided a method for testing a piezoelectric/electrostrictive actuator, wherein the displacement of a piezoelectric/electrostrictive actuator is estimated on the basis of the relations between one or more frequency characteristic values selected from the group consisting of the heights and areas of the peaks of the resonance waveforms and the difference of the maximum and minimum of the first order or first to higher orders of the resonance frequency characteristic values of the piezoelectric/electrostrictive actuator and the k-th order (k=1 to 4) of the first or first to higher orders of resonance frequencies. According to this piezoelectric/electrostrictive actuator testing method, a piezoelectric/electrostrictive actuator can be tested with high precision without actually driving the same as a product and without being accompanied by any disassembly/breakage.

7 Claims, 10 Drawing Sheets

METHOD FOR TESTING PIEZOELECTRIC/ELECTROSTRICTIVE DEVICE, TESTING APPARATUS, AND METHOD FOR ADJUSTING PIEZOELECTRIC/ELECTROSTRICTIVE DEVICE

FIELD OF THE INVENTION

The present invention relates to a method for testing a piezoelectric/electrostrictive device realizing high precision, a testing apparatus, and a method for adjusting a piezoelectric/electrostrictive device.

BACKGROUND ART

In recent years, a displacement control device has been desired for adjusting an optical path length or a position by the submicron in fields of optics, precision machinery, semiconductor manufacturing, and the like. To respond to this, development has been promoted of piezoelectric/electrostrictive devices such as a piezoelectric/electrostrictive actuator utilizing strain based on the inverse piezoelectric effect, the electrostrictive effect, or the like caused when an electric field is applied to a ferroelectric body or an antiferroelectric body and a piezoelectric/electrostrictive sensor utilizing charge generation caused when stress is applied to a ferroelectric body/antiferroelectric body on the basis of a similar effect.

For example, an embodiment of a piezoelectric/electrostrictive actuator has a structure where a piezoelectric/electrostrictive actuating portion obtained by laminating a lower electrode, a piezoelectric/electrostrictive body, and an upper electrode in sequence on a surface of a ceramic substrate formed by unitarily forming a thick support portion having a cavity and a vibration portion covering the cavity. In such a piezoelectric/electrostrictive actuator, when an electric field is generated between the upper electrode and the lower electrode, a piezoelectric/electrostrictive body of a piezoelectric/electrostrictive material is deformed to generate a displacement in a vertical direction in the vibration portion. By the function of displacing the vibration portion, the piezoelectric/electrostrictive actuator is applied as an actuator portion of a precision equipment. Such a piezoelectric/electrostrictive actuator controls contact or noncontact of a switch or controls fluid as a micro pump by, for example, transforming the vibration portion vertically.

In the case that a piezoelectric/electrostrictive actuator as described above is used as an actuator portion or the like of a switch or a micro pump, when the displacement is not large enough, a stroke is insufficient in the switch, and it does not function as a switch, or a fluid extrusion amount is insufficient in the micro pump or no fluid can be extruded in some cases. In addition, for example, in the case of using a plurality of piezoelectric/electrostrictive actuators together, when the displacement is varied among the actuators, contact or non-contact motion becomes unstable, or a fluid extrusion amount becomes unstable to deteriorate quality of the switch or the micro pump.

Therefore, quality control is performed so that the displacement of each vibration portion may have at least a certain amount and be uniform when the same voltage is applied (same electric field is generated).

Incidentally, a prior art document of the same technical field is a WO No. 05/104258 pamphlet.

An example of a testing method performed when piezoelectric/electrostrictive actuators are shipped as products is a method for directly testing the displacement of the vibration portion by the use of a laser Doppler vibrometer or the like. In addition, there has been known a method for testing the size and uniformity of the displacement when the same voltage is applied (same electric field is caused) by measuring capacitance of a piezoelectric/electrostrictive body to be used to resemble a condenser in a manufacturing step of a piezoelectric/electrostrictive actuator.

However, the former method requires high costs when the test is performed for all the lots of the piezoelectric/electrostrictive actuators manufactured. In addition, the latter method does not always have high testing precision because the constituents other than the piezoelectric/electrostrictive actuating portion of the piezoelectric/electrostrictive actuator are not reflected to the test.

Further, in a recent piezoelectric/electrostrictive actuator, because of the advance of miniaturization, slight slippage or variance of the size more seriously influences on the properties, and observation of a cross section with the destruction is necessary to test the slippage or variance of the size. In such a case, it is impossible to directly test the products to be shipped.

Such a problem is likewise caused also in a piezoelectric/electrostrictive sensor where the uniform sensor sensitivity is required in the case of the same design and specification.

SUMMARY OF THE INVENTION

The present invention has been made in view of such problems and aims to provide a means capable of testing a piezoelectric/electrostrictive device (piezoelectric/electrostrictive actuator and piezoelectric/electrostrictive sensor) highly precisely without actually driving the device as a product and without being accompanied by any disassembly/breakage.

As a result of repeated studies, it was found out that the aforementioned problems can be solved by a means shown below, which lead to the present invention. Specifically, the present invention provides the following means.

That is, in the first place, according to the present invention, there is provided a method for testing a piezoelectric/electrostrictive actuator, wherein the displacement of a piezoelectric/electrostrictive actuator is estimated on the basis of the relations ($\alpha 0$) between one or more frequency characteristic values selected from the group consisting of the heights and areas of the peaks of the resonance waveforms and the difference of the maximum and minimum of the first order or first to higher orders of the resonance frequency characteristic values of the piezoelectric/electrostrictive actuator and the k-th order ($k=1$ to 4) of the first or first to higher orders of resonance frequencies.

This relation ($\alpha 0$) can be expressed by, for example, the following formula (1).

[Formula 1]

$$\text{Estimated displacement standard value } MV = \sum_{j=1}^{m} \frac{\sum_{j=m}^{n} Rj}{f_m^k} \quad (1)$$

($i=1, 2, 3 \ldots m$, $j=1, 2, 3 \ldots n$ (where $n \geq m$), $k=1$ to 4)
R: resonance frequency characteristic values
f: resonance frequency In addition, the aforementioned relation ($\alpha 0$) can be expressed by, for example, the following formula (2).

[Formula 2]

$$\text{Estimated displacement standard value } MV = \sum_{i=1}^{m} \frac{R_i}{f_i^k} \quad (2)$$

(i=1, 2, 3 ... m, k=1 to 4)
R: resonance frequency characteristic values
f: resonance frequency In a method for testing a piezoelectric/electrostrictive actuator of the present invention, it is preferable that the aforementioned relation (α0) is a relation (α1) of dividing the one or more frequency characteristic values selected from the group consisting of the heights and areas of the peaks of the resonance waveforms and the difference of the maximum and minimum of the first order of the resonance frequency characteristic values of the piezoelectric/electrostrictive actuator by the k-th order (k=1 to 4) of the first order of resonance frequency to estimate the displacement of the piezoelectric/electrostrictive actuator by the calculated value obtained by the division.

The relation (α1), which is a subordinate concept of the relation (α0), can be expressed by, for example, the following formula (3). This is the case of m=1 (only the first term) and n=m (only the first term) in the formula (1).

[Formula 3]

$$\text{Estimated displacement standard value } MV = \frac{R_1}{f_1^k} \quad (3)$$

In a method for testing a piezoelectric/electrostrictive actuator of the present invention, it is preferable that the aforementioned relation (α0) is a relation (α2) of dividing a sum of the one or more frequency characteristic values selected from the group consisting of the heights and areas of the peaks of the resonance waveforms and the difference of the maximum and minimum of the first to higher orders of the resonance frequency characteristic values of the piezoelectric/electrostrictive actuator by the k-th order (k=1 to 4) of the first order of resonance frequency to estimate the displacement of the piezoelectric/electrostrictive actuator by the calculated value obtained by the division.

The relation (α2), which is a subordinate concept of the relation (α0), can be expressed by, for example, the following formula (4). This is the case of m=1 (only the first term) and n=3 in the formula (1).

[Formula 4]

$$\text{Estimated displacement standard value } MV = \frac{R_1 + R_2 + R_3}{f_1^k} \quad (4)$$

In a method for testing a piezoelectric/electrostrictive actuator of the present invention, it is preferable that the aforementioned relation (α0) is a relation (α3) of dividing the one or more frequency characteristic values selected from the group consisting of the heights and areas of the peaks of the resonance waveforms and the difference of the maximum and minimum of the resonance frequency characteristic value for each of the resonances of the first to higher orders of the piezoelectric/electrostrictive actuator by the k-th order (k=1 to 4) of resonance frequency and obtaining the sum of the values for each of the resonances to estimate the displacement of the piezoelectric/electrostrictive actuator by the calculated value obtained by the sum.

The relation (α3) which is a subordinate concept of the relation (α0) can be expressed by, for example, the following formula (5). This is the case of m=3 in the formula (2).

[Formula 5]

$$\text{Estimated displacement standard value } MV = \frac{R_1}{f_1^k} + \frac{R_2}{f_2^k} + \frac{R_3}{f_3^k} \quad (5)$$

In a method for testing a piezoelectric/electrostrictive actuator of the present invention, it is preferable that the displacement of the piezoelectric/electrostrictive actuator is estimated by a value obtained by further multiplying any of the aforementioned calculated values by the capacitance of the piezoelectric/electrostrictive actuator.

Next, according to the present invention, there is provided an apparatus for testing piezoelectric/electrostrictive actuator, wherein the apparatus is provided with a means for estimating the displacement of the piezoelectric/electrostrictive actuator on the basis of the relations (α0) between one or more frequency characteristic values selected from the group consisting of the heights and areas of the peaks of the resonance waveforms and the difference of the maximum and minimum of the first order or first to higher orders of the resonance frequency characteristic values of the piezoelectric/electrostrictive actuator and the k-th order (k=1 to 4) of the first or first to higher orders of resonance frequencies. The aforementioned means can be realized by, for example, a computer and a software. That is, a testing apparatus of a piezoelectric/electrostrictive actuator of the present invention is a computer with a program for estimating the displacement of the piezoelectric/electrostrictive actuator on the basis of the relations (α0) between one or more frequency characteristic values selected from the group consisting of the heights and areas of the peaks of the resonance waveforms and the difference of the maximum and minimum of the first order or first to higher orders of the resonance frequency characteristic values of the piezoelectric/electrostrictive actuator and the k-th order (k=1 to 4) of the first or first to higher orders of resonance frequencies. Since the first order or first to higher orders of the resonance frequency characteristic values and the first order or first to higher orders of resonance frequencies can be measured by the network analyzer described later or the like, a testing apparatus for a piezoelectric/electrostrictive actuator of the present invention can be constituted of, for example, a network analyzer and the aforementioned computer with the program, and a method for testing a piezoelectric/electrostrictive actuator of the present invention can be performed by a testing apparatus for a piezoelectric/electrostrictive actuator of the present invention.

In an apparatus for testing a piezoelectric/electrostrictive actuator of the present invention, it is preferable that the aforementioned relation (α0) is a relation (α1) of dividing the one or more frequency characteristic values selected from the group consisting of the heights and areas of the peaks of the resonance waveforms and the difference of the maximum and minimum of the first order of the resonance frequency characteristic values of the piezoelectric/electrostrictive actuator by the k-th order (k=1 to 4) of the first order of resonance frequency and that the apparatus is provided with a means for estimating the displacement of the piezoelectric/electrostrictive actuator by the calculated value obtained by the division. Such a means can be realized by a computer and a software.

In an apparatus for testing a piezoelectric/electrostrictive actuator of the present invention, it is preferable that the aforementioned relation (α0) is a relation (α2) of dividing a sum of the one or more frequency characteristic values selected from the group consisting of the heights and areas of the peaks of the resonance waveforms and the difference of the maximum and minimum of the first to higher orders of the resonance frequency characteristic values of the piezoelectric/electrostrictive actuator by the k-th order (k=1 to 4) of the first order of resonance frequency and that the apparatus is provided with a means for estimating the displacement of the piezoelectric/electrostrictive actuator by the calculated value obtained by the division. Such a means can be realized by a computer and a software.

In an apparatus for testing a piezoelectric/electrostrictive actuator of the present invention, it is preferable that the aforementioned relation (α0) is a relation (α3) of dividing the one or more frequency characteristic values selected from the group consisting of the heights and areas of the peaks of the resonance waveforms and the difference of the maximum and minimum of the resonance frequency characteristic value for each of the resonances of the first to higher orders of the piezoelectric/electrostrictive actuator by the k-th order (k=1 to 4) of resonance frequency and obtaining the sum of the values for each of the resonances and that the apparatus is provided with a means for estimating the displacement of the piezoelectric/electrostrictive actuator by the calculated value obtained by the sum. Such a means can be realized by a computer and a software.

In an apparatus for testing a piezoelectric/electrostrictive actuator of the present invention, it is preferable that the apparatus is provided with a means for estimating the displacement of the piezoelectric/electrostrictive actuator by a value obtained by further multiplying the calculated value by the capacitance of the piezoelectric/electrostrictive actuator. Such a means can be realized by a computer and a software.

Next, according to the present invention, there is provided a method for testing a piezoelectric/electrostrictive sensor, wherein the detection sensitivity of a piezoelectric/electrostrictive sensor is estimated on the basis of the relations (α10) between one or more frequency characteristic values selected from the group consisting of the heights and areas of the peaks of the resonance waveforms and the difference of the maximum and minimum of the first order or first to higher orders of the resonance frequency characteristic values of the piezoelectric/electrostrictive sensor and the k-th order (k=1 to 4) of the first or first to higher orders of resonance frequencies.

The relation (α10) can be expressed by, for example, the following formula (6).

[Formula 6]

$$\text{Estimated detection sensitivity standard value } ST = \sum_{i=1}^{m} \frac{\sum_{j=m}^{n} Rj}{f_m^k} \quad (6)$$

(i=1, 2, 3 ... m, j=1, 2, 3 ... n (where n≧m), k=1 to 4)
R: resonance frequency characteristic values
f: resonance frequency In addition, the aforementioned relation (α10) can be expressed by, for example, the following formula (7).

[Formula 7]

$$\text{Estimated detection sensitivity standard value } ST = \sum_{i=1}^{m} \frac{R_i}{f_i^k} \quad (7)$$

(i=1, 2, 3 ... m, k=1 to 4)
R: resonance frequency characteristic values
f: resonance frequency In a method for testing a piezoelectric/electrostrictive sensor of the present invention, it is preferable that the relation (α10) is a relation (α11) of dividing the one or more frequency characteristic values selected from the group consisting of the heights and areas of the peaks of the resonance waveforms and the difference of the maximum and minimum of the first order of the resonance frequency characteristic values of the piezoelectric/electrostrictive sensor by the k-th order (k=1 to 4) of the first order of resonance frequency to estimate the detection sensitivity of the piezoelectric/electrostrictive sensor by the calculated value obtained by the division.

The relation (α11), which is a subordinate concept of the relation (α10), can be expressed by, for example, the following formula (8). This is the case of m=1 (only the first term) and n=m (only the first term) in the formula (6).

[Formula 8]

$$\text{Estimated detection sensitivity standard value } ST = \frac{R_1}{f_1^k} \quad (8)$$

In a method for testing a piezoelectric/electrostrictive sensor of the present invention, it is preferable that the relation (α10) is a relation (α12) of dividing a sum of the one or more frequency characteristic values selected from the group consisting of the heights and areas of the peaks of the resonance waveforms and the difference of the maximum and minimum of the first to higher orders of the resonance frequency characteristic values of the piezoelectric/electrostrictive sensor by the k-th order (k=1 to 4) of the first order of resonance frequency to estimate the detection sensitivity of the piezoelectric/electrostrictive sensor by the calculated value obtained by the division.

The relation (α12), which is a subordinate concept of the relation (α10), can be expressed by, for example, the following formula (9). This is the case of m=1 (only the first term) and n=3 in the formula (6).

[Formula 9]

$$\text{Estimated detection sensitivity standard value } ST = \frac{R_1 + R_2 + R_3}{f_1^k} \quad (9)$$

In a method for testing a piezoelectric/electrostrictive sensor of the present invention, it is preferable that the relation (α10) is a relation (α13) of dividing the one or more frequency characteristic values selected from the group consisting of the heights and areas of the peaks of the resonance waveforms and the difference of the maximum and minimum of the resonance frequency characteristic value for each of the resonances of the first to higher orders of the piezoelectric/electrostrictive sensor by the k-th order (k=1 to 4) of resonance frequency and obtaining the sum of the values for each of the resonances to estimate the detection sensitivity of the piezoelectric/electrostrictive sensor by the calculated value obtained by the sum.

The relation (α13), which is a subordinate concept of the relation (α10), can be expressed by, for example, the following formula (10). This is the case of m=3 in the formula (7).

[Formula 10]

$$\text{Estimated detection sensitivity standard value } ST = \frac{R_1}{f_1^k} + \frac{R_2}{f_2^k} + \frac{R_3}{f_3^k} \quad (10)$$

In a method for testing a piezoelectric/electrostrictive sensor of the present invention, it is preferable that the detection sensitivity of the piezoelectric/electrostrictive sensor is estimated by a value obtained by further multiplying any of the aforementioned calculated values by the capacitance of the piezoelectric/electrostrictive sensor.

Next, according to the present invention, there is provided an apparatus for testing a piezoelectric/electrostrictive sensor, provided with a means for estimating the detection sensitivity of a piezoelectric/electrostrictive sensor on the basis of the relations (α10) between one or more frequency characteristic values selected from the group consisting of the heights and areas of the peaks of the resonance waveforms and the difference of the maximum and minimum of the first order or first to higher orders of the resonance frequency characteristic values of the piezoelectric/electrostrictive sensor and the k-th order (k=1 to 4) of the first or first to higher orders of resonance frequencies. The aforementioned means can be realized by, for example, a computer and a software. That is, a testing apparatus of a piezoelectric/electrostrictive sensor of the present invention is a computer with a program for estimating the detection sensitivity of the piezoelectric/electrostrictive sensor on the basis of the relations (α10) between one or more frequency characteristic values selected from the group consisting of the heights and areas of the peaks of the resonance waveforms and the difference of the maximum and minimum of the first order or first to higher orders of the resonance frequency characteristic values of the piezoelectric/electrostrictive sensor and the k-th order (k=1 to 4) of the first or first to higher orders of resonance frequencies. Since the first order or first to higher orders of the resonance frequency characteristic values and the first order or first to higher orders of resonance frequencies can be measured by the network analyzer described later or the like, a testing apparatus for a piezoelectric/electrostrictive sensor of the present invention can be constituted of, for example, a network analyzer and the aforementioned computer with the program, and a method for testing a piezoelectric/electrostrictive sensor of the present invention can be performed by a testing apparatus for a piezoelectric/electrostrictive sensor of the present invention.

In an apparatus for testing a piezoelectric/electrostrictive sensor of the present invention, it is preferable that the relation (α10) is a relation (α11) of dividing the one or more frequency characteristic values selected from the group consisting of the heights and areas of the peaks of the resonance waveforms and the difference of the maximum and minimum of the first order of the resonance frequency characteristic values of the piezoelectric/electrostrictive sensor by the k-th order (k=1 to 4) of the first order of resonance frequency and that the apparatus is provided with a means for estimating the detection sensitivity of the piezoelectric/electrostrictive sensor by the calculated value obtained by the division. Such a means can be realized by a computer and a software.

In an apparatus for testing a piezoelectric/electrostrictive sensor of the present invention, it is preferable that the aforementioned relation (α10) is a relation (α12) of dividing a sum of the one or more frequency characteristic values selected from the group consisting of the heights and areas of the peaks of the resonance waveforms and the difference of the maximum and minimum of the first to higher orders of the resonance frequency characteristic values of the piezoelectric/electrostrictive sensor by the k-th order (k=1 to 4) of the first order of resonance frequency and that the apparatus is provided with a means for estimating the detection sensitivity of the piezoelectric/electrostrictive sensor by the calculated value obtained by the division. Such a means can be realized by a computer and a software.

In an apparatus for testing a piezoelectric/electrostrictive sensor of the present invention, it is preferable that the aforementioned relation (α10) is a relation (α13) of dividing the one or more frequency characteristic values selected from the group consisting of the heights and areas of the peaks of the resonance waveforms and the difference of the maximum and minimum of the resonance frequency characteristic value for each of the resonances of the first to higher orders of the piezoelectric/electrostrictive sensor by the k-th order (k=1 to 4) of resonance frequency and obtaining the sum of the values for each of the resonances and that the apparatus is provided with a means for estimating the detection sensitivity of the piezoelectric/electrostrictive sensor by the calculated value obtained by the sum. Such a means can be realized by a computer and a software.

In an apparatus for testing a piezoelectric/electrostrictive sensor of the present invention, it is preferable that the apparatus is provided with a means for estimating the detection sensitivity of the piezoelectric/electrostrictive sensor by a value obtained by further multiplying the calculated value by the capacitance of the piezoelectric/electrostrictive sensor. Such a means can be realized by a computer and a software.

In the present specification, piezoelectric/electrostrictive actuators and piezoelectric/electrostrictive sensors are collectively referred to as piezoelectric/electrostrictive devices. In addition, both the method for inspecting a piezoelectric/electrostrictive actuator and the method for inspecting a piezoelectric/electrostrictive sensor may be referred to as methods for inspecting piezoelectric/electrostrictive devices. Both the apparatus for inspecting a piezoelectric/electrostrictive actuator and the apparatus for inspecting a piezoelectric/electrostrictive sensor may be referred to as apparatuses for inspecting piezoelectric/electrostrictive devices. All of them may be referred to as inspection methods and inspection apparatuses for piezoelectric/electrostrictive devices of the present invention.

The resonance frequency and the resonance frequency characteristic value used in a method and an apparatus for testing a piezoelectric/electrostrictive device of the present invention is a resonance frequency and a resonance frequency characteristic value of an electrical constant of impedance, admittance (conductance, susceptance), or the like. The resonance frequency and the resonance frequency characteristic value can be measured at a high speed at low costs by the use of a network analyzer or an impedance analyzer. The (first to higher orders of) the resonance frequency characteristic value used in a method or an apparatus for testing a piezoelectric/electrostrictive device of the present invention is at least one (resonance) frequency characteristic value selected from the group consisting of the heights of the peaks of the resonance waveforms (of the first to higher orders), areas (of the resonance waveforms of the first to higher orders), and the difference of the maximum and minimum (of the resonance waveforms of the first to higher orders), and these heights of the peaks, areas, and difference of the maximum and minimum can be obtained by a chart with frequency as an axis of abscissas and with, for example, conductance (or impedance, susceptance, or the like) as an axis of ordinate. The chart can be obtained by the aforementioned network analyzer or impedance analyzer.

In a method and an apparatus for testing a piezoelectric/electrostrictive actuator of the present invention, with regard to a piezoelectric/electrostrictive actuator having a piezoelectric/electrostrictive body and two or more electrodes as the constituents, since the displacement of a piezoelectric/electrostrictive actuator is estimated not by using only the capacitance loaded on the piezoelectric/electrostrictive body as a part of the piezoelectric/electrostrictive actuator, but estimated on the basis of the relations between one or more frequency characteristic values selected from the group consisting of the heights and areas of the peaks of the resonance waveforms and the difference of the maximum and minimum of the first order or first to higher orders of the resonance frequency characteristic values of the entire piezoelectric/electrostrictive actuator and the k-th order (k=1 to 4) of the first or first to higher orders of resonance frequencies, the test can be performed with high precision without relying on experiences. In addition, because of a nondestructive test, more precise good or bad decision can be performed quickly. Therefore, error of shipping undesirable products can be inhibited.

In a method and an apparatus for testing a piezoelectric/electrostrictive sensor of the present invention, with regard to a piezoelectric/electrostrictive sensor having a piezoelectric/electrostrictive body and two or more electrodes as the constituents, since the detection sensitivity of a piezoelectric/electrostrictive sensor is estimated not by using only the capacitance loaded on the piezoelectric/electrostrictive body as a part of the piezoelectric/electrostrictive sensor, but estimated on the basis of the relations between one or more frequency characteristic values selected from the group consisting of the heights and areas of the peaks of the resonance waveforms and the difference of the maximum and minimum of the first order or first to higher orders of the resonance frequency characteristic values of the entire piezoelectric/electrostrictive sensor and the k-th order (k=1 to 4) of the first or first to higher orders of resonance frequencies, the test can be performed with high precision without relying on experiences. In addition, because of a nondestructive test, more precise good or bad decision can be performed quickly. Therefore, error of shipping undesirable products can be inhibited.

Next, according to the present invention, there is provided a method for adjusting a piezoelectric/electrostrictive actuator, comprising:

estimating the displacements of a plurality of piezoelectric/electrostrictive actuators by the use of a method for testing any one of the aforementioned piezoelectric/electrostrictive actuators, and trimming an upper electrode with regard to at least some of the plurality of actuators to adjust the displacement of the piezoelectric/electrostrictive actuators uniformly. By thus trimming the upper electrode, it is possible to adjust also the generation force of the piezoelectric/electrostrictive actuator.

In a method for adjusting a piezoelectric/electrostrictive actuator of the present invention, it is preferable that the trimming is performed by a processing method by laser irradiation, electron beam irradiation, cutting, or the like. In particular, a processing method by laser irradiation is suitably used because a beam wavelength can be selected in accordance with characteristics of the material to be removed.

In a method for adjusting a piezoelectric/electrostrictive actuator of the present invention, since the trimming forms at least one predetermined pattern in the vicinity of the central portion of the upper electrode where the maximum displacement is generated, it is possible to obtain the change of the displacement by a small trimming amount. As the predetermined pattern used here, a circular through-hole (cross section perpendicular to the axial direction), a slit, or the like can be considered. In particular, in the processing method by laser irradiation, since the processing shape is easily obtained stably to be able to enhance resolution of a removal area, a circular through-hole is suitably employed. In addition, since resolution of the removal area can be enhanced effectively by the smaller number of trimming patterns, when the pattern is a circular through-hole, the through-hole preferably has a different diameter. Further, when the aforementioned pattern is a slit, the slit preferably has a different width.

In a method for adjusting a piezoelectric/electrostrictive actuator of the present invention, it is preferable that the displacements of a plurality of piezoelectric/electrostrictive actuators is estimated by the use of a method for testing any of the aforementioned piezoelectric/electrostrictive actuator and that a piezoelectric/electrostrictive body is trimmed with regard to at least some of the plurality of piezoelectric/electrostrictive actuators to adjust the displacement of the piezoelectric/electrostrictive actuators uniformly. By trimming the piezoelectric/electrostrictive body, it is possible to adjust mechanical rigidity of the piezoelectric/electrostrictive actuator. That is, since the displacement can be adjusted without changing an electric constant such as capacitance or equivalent parallel resistance of the piezoelectric/electrostrictive actuator, it is possible to suppress the adjustment amount on the driving circuit side of the piezoelectric/electrostrictive actuator to the minimum.

In a method for adjusting a piezoelectric/electrostrictive actuator of the present invention, it is preferable that both the piezoelectric/electrostrictive body and the upper electrode are trimmed with regard to at least some of the plurality of piezoelectric/electrostrictive actuators. Since the generation force and the mechanical rigidity of the piezoelectric/electrostrictive actuator can simultaneously be adjusted by trimming both the piezoelectric/electrostrictive body and the upper electrode, it is possible to adjust the displacement of the piezoelectric/electrostrictive actuator on a grand scale.

In a method for adjusting a piezoelectric/electrostrictive actuator of the present invention, it is preferable that the trimming is performed in at least a portion where the maximum displacement of the piezoelectric/electrostrictive actuator is generated. This enables to adjust the displacement efficiently with a small trimming amount or trimming area.

In a method for adjusting a piezoelectric/electrostrictive actuator of the present invention, it is preferable that the trimming is performed in a portion (the vicinity of the so called side) having the maximum amplitude in the first order of the resonance mode. This makes the probability of inducing another vibration mode low, and a vibration mode similar to that of a piezoelectric/electrostrictive actuator without trimming can be realized. As a result, it becomes possible to adjust the displacement where the change in the first or higher orders of the resonance frequency is suppressed to the minimum.

Next, according to the present invention, there is provided a piezoelectric/electrostrictive actuator obtained by adjusting the displacement uniformly by using the aforementioned method for adjusting a piezoelectric/electrostrictive actuator.

Next, according to the present invention, it is preferable that the detection sensitivity of the plurality of piezoelectric/electrostrictive sensors is estimated by the use of any of the aforementioned methods for testing a piezoelectric/electrostrictive sensor and that the upper electrode of each of at least some of the plurality of piezoelectric/electrostrictive sensors is trimmed to adjust the detection sensitivity of the plurality of piezoelectric/electrostrictive sensors uniformly. By thus trimming the upper electrode, it is possible to adjust the generation force upon driving the piezoelectric/electrostrictive sensor, and it is possible to adjust the displacement upon driving the piezoelectric/electrostrictive sensor. Therefore, it becomes possible to adjust the detection sensitivity of the piezoelectric/electrostrictive sensor.

The detection sensitivity of a piezoelectric/electrostrictive sensor in the present specification means the performance of the piezoelectric/electrostrictive sensor and a ratio of output to input. For example, when the piezoelectric/electrostrictive sensor is a viscosity sensor for a fluid, the electric charge generation caused when the fluid applies stress to the piezoelectric/electrostrictive sensor can be detected, and the ratio of the electric charge generation amount to the viscosity is the detection sensitivity in this case. By adjusting the displacement upon driving the fluid sensor, it becomes possible to make the volume and speed of the fluid to be activated uniform, thereby reducing the measurement error.

In a method for adjusting a piezoelectric/electrostrictive sensor of the present invention, it is preferable that the trimming is performed by a processing method by laser irradiation, electron beam irradiation, cutting, or the like. In particular, a processing method by laser irradiation is suitably used because a beam wavelength can be selected in accordance with characteristics of the material to be removed.

In a method for adjusting a piezoelectric/electrostrictive sensor of the present invention, since the trimming forms at least one predetermined pattern in the vicinity of the central portion of the upper electrode where the maximum displacement is generated, it is possible to obtain a large change of detention voltage by a small trimming amount. As the predetermined pattern used here, a circular through-hole (cross section perpendicular to the axial direction), a slit, or the like can be considered. In particular, in the processing method by laser irradiation, since the processing shape is easily obtained stably to be able to enhance resolution of a removal area, a circular through-hole is suitably employed. In addition, since resolution of the removal area can be enhanced effectively by the smaller number of trimming patterns, when the pattern is a circular through-hole, the through-hole preferably has a different diameter. Further, when the aforementioned pattern is a slit, the slit preferably has a different width.

In a method for adjusting a piezoelectric/electrostrictive sensor of the present invention, it is preferable that the detective sensitivity of a plurality of piezoelectric/electrostrictive sensors is estimated by the use of any of the aforementioned methods for testing a piezoelectric/electrostrictive sensor and that a piezoelectric/electrostrictive body is trimmed with regard to at least some of the plurality of piezoelectric/electrostrictive sensors on the basis of the estimated detection sensitivity of each of the piezoelectric/electrostrictive sensors to adjust the detection sensitivity of the piezoelectric/electrostrictive sensors uniformly. By thus trimming the piezoelectric/electrostrictive body, it is possible to adjust mechanical rigidity of the piezoelectric/electrostrictive sensor. Therefore, it is possible to adjust the displacement upon driving the piezoelectric/electrostrictive sensor, and it is possible to adjust the detection sensitivity of the piezoelectric/electrostrictive sensor. That is, since the detection sensitivity upon driving the piezoelectric/electrostrictive sensor can be adjusted without changing an electric constant such as capacitance or equivalent parallel resistance of the piezoelectric/electrostrictive sensor, it is possible to suppress the adjustment amount on the driving circuit side of the piezoelectric/electrostrictive sensor to the minimum.

In a method for adjusting a piezoelectric/electrostrictive sensor of the present invention, it is preferable that the piezoelectric/electrostrictive body and the upper electrode are trimmed with regard to at least some of the plurality of piezoelectric/electrostrictive sensors. Since the generation force and the mechanical rigidity of the piezoelectric/electrostrictive sensor can simultaneously be adjusted by trimming both the piezoelectric/electrostrictive body and the upper electrode, it is possible to adjust the detection sensitivity of the piezoelectric/electrostrictive sensor on a grand scale.

In a method for adjusting a piezoelectric/electrostrictive sensor of the present invention, it is preferable that the trimming is performed in at least a portion where the maximum displacement of the piezoelectric/electrostrictive sensor is generated. Since this enables to adjust the generation force and mechanical rigidity upon driving the piezoelectric/electrostrictive sensor efficiently with a small trimming amount or trimming area, as a result, it is possible to adjust the detection sensitivity of the piezoelectric/electrostrictive sensor efficiently.

In a method for adjusting a piezoelectric/electrostrictive sensor of the present invention, it is preferable that the trimming is performed in a portion having the maximum amplitude in the first order of the resonance mode. This makes the probability of inducing another vibration mode, and a vibration mode similar to that of a piezoelectric/electrostrictive actuator without trimming can be realized. As a result, it becomes possible to adjust the detection sensitivity with suppressing the change in the first or higher orders of the resonance frequency to the minimum.

Next, according to the present invention, there is provided a piezoelectric/electrostrictive sensor obtained by adjusting the detection sensitivity uniformly by using the aforementioned method for adjusting a piezoelectric/electrostrictive sensor.

DESCRIPTION OF REFERENCE NUMERALS USED IN THE DRAWING FIGURES

Figure 1:
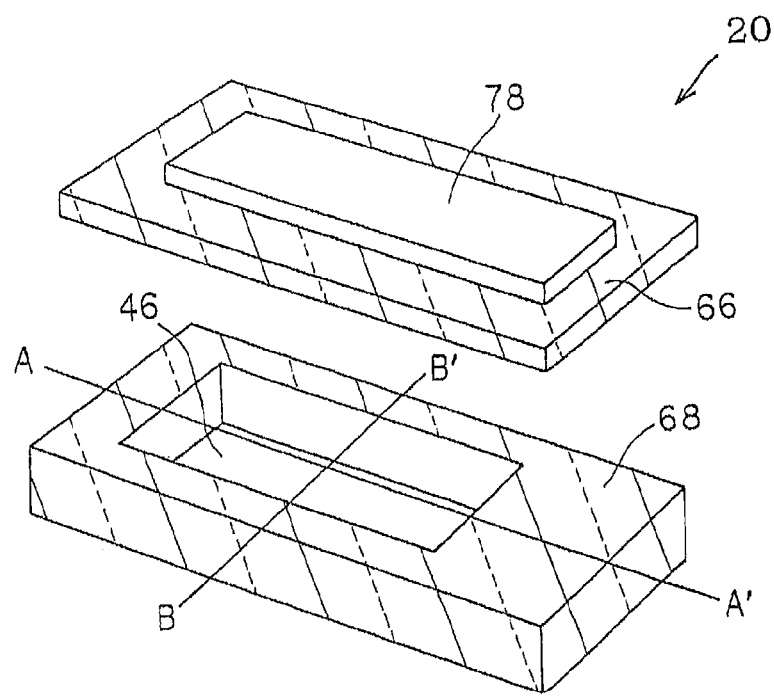
FIG. 1 is a view showing an example of a piezoelectric/electrostrictive actuator and perspective view showing the vibration portion and the support portion separately.

20, 30, 40, 50, 60, 70, 80, 90: piezoelectric/electrostrictive actuator; 44: Substrate; 46: cavity; 66: vibration portion; 68: support portion; 73: intermediate electrode; 75: upper electrode; 77: lower electrode; 78: piezoelectric/electrostrictive actuating portion 79: piezoelectric/electrostrictive body; 81, 84, 85, 86: circular through-hole (through-hole of upper electrode); 82, 87, 88, 89: slit (slit of upper electrode); 83: slit (slit of piezoelectric/electrostrictive body); 120: micro switch; 121: terminal board; and 122: LCR meter.

DETAILED DESCRIPTION OF THE INVENTION

Hereinbelow, embodiments of the present invention will be described with suitably referring to drawings. However, the present invention should not be construed with limiting to these, and various changes, modifications, and improvements may be made on the basis of knowledge of a person of ordinary skill in the art as long as they do not deviate from the scope of the present invention. For example, though the drawings show preferable embodiments of the present invention, the present invention is not limited by the modes or information shown in the drawings. When the present invention is carried out or investigated, the means which is the same as or equivalent to the means described in the present specification can be applied. However, a suitable means is the means described below.

Figure 2:
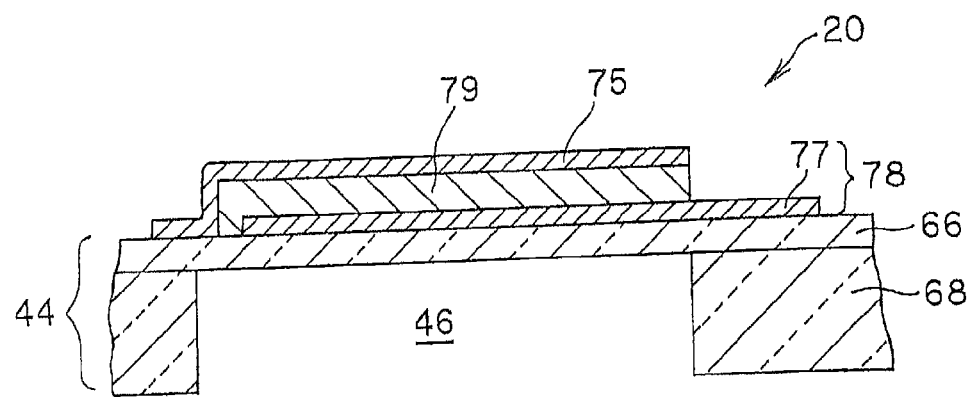
FIG. 2 is a cross-sectional view showing the A-A' cross section including the vibration portion and piezoelectric/electrostrictive actuating portion of the piezoelectric/electrostrictive actuator shown in FIG. 1.
Figure 3:
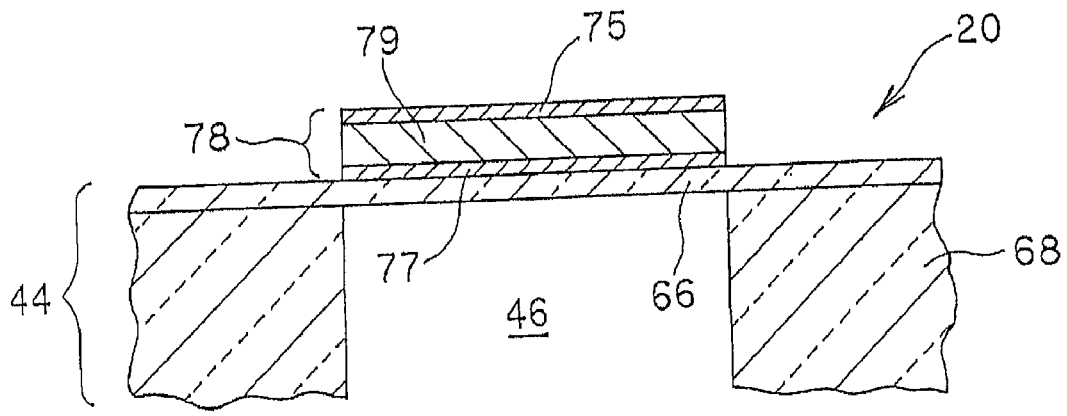
FIG. 3 is a cross-sectional view showing the B-B' cross section including the vibration portion and the piezoelectric/electrostrictive actuating portion of the piezoelectric/electrostrictive actuator shown in FIG. 1.
Figure 4:
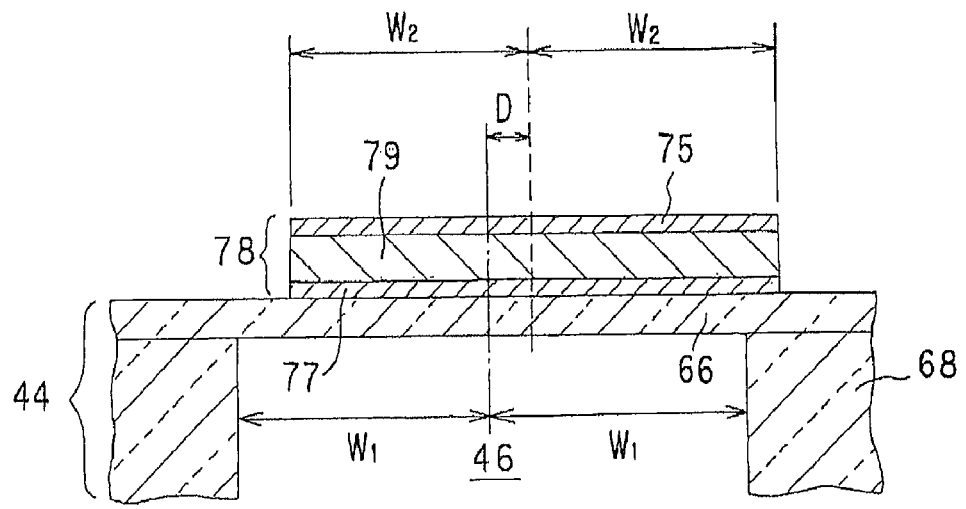
FIG. 4 is a cross-sectional view showing an example of a piezoelectric/electrostrictive actuator where the substrate and the piezoelectric/electrostrictive actuating portion are shifted from each other and view showing a cross section corresponding with FIG. 3.
Figure 5:
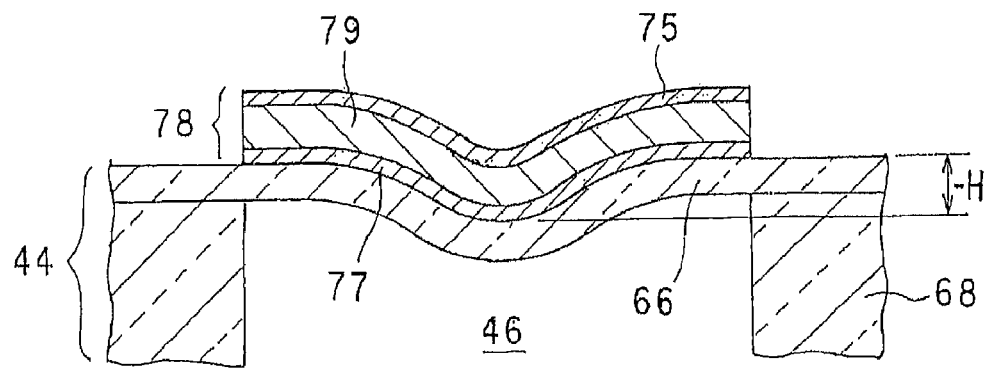
FIG. 5 is a cross-sectional view showing a piezoelectric/electrostrictive actuator where the vibration portion has a downward undulation (in the figure) and view showing a cross section corresponding with FIG. 3.

In the first place, a piezoelectric/electrostrictive actuator capable of serving as a target of the method and apparatus for testing a piezoelectric/electrostrictive actuator of the present invention. FIGS. 1, 2, 3, 4 and 5 are views each showing an example of a piezoelectric/electrostrictive actuator. FIG. 1 is a perspective view where the vibration portion 66 and the support portion 68 are separated, FIG. 2 is a cross-sectional view showing the A-A' cross section including the vibration portion 66 and piezoelectric/electrostrictive actuating portion 78 of the piezoelectric/electrostrictive actuator shown in FIG. 1, and FIG. 3 is a cross-sectional view showing the B-B' cross section likewise. The piezoelectric/electrostrictive actuator 20 in the figure has a substrate 44 and a piezoelectric/electrostrictive actuating portion 78. The substrate 44 is obtained by unitarily forming a thick support portion 68 having a cavity 46 and a vibration portion 66 covering the cavity 46. The piezoelectric/electrostrictive actuating portion 78 has a piezoelectric/electrostrictive body 79, the upper electrode 75 formed on one surface, and the lower electrode 77 formed on the other surface and is disposed on one surface of the substrate 44 in such a manner that lower electrode 77 contacts the vibration portion 66.

In the piezoelectric/electrostrictive actuator 20, when an electric field is generated between the upper electrode 75 and the lower electrode 77, the displacement is generated in the piezoelectric/electrostrictive body 79 of a piezoelectric/electrostrictive material to transform the vibration portion 66. By this function, the piezoelectric/electrostrictive actuator 20 is applied as an actuator portion for, for example, a precision equipment.

Figure 6A:
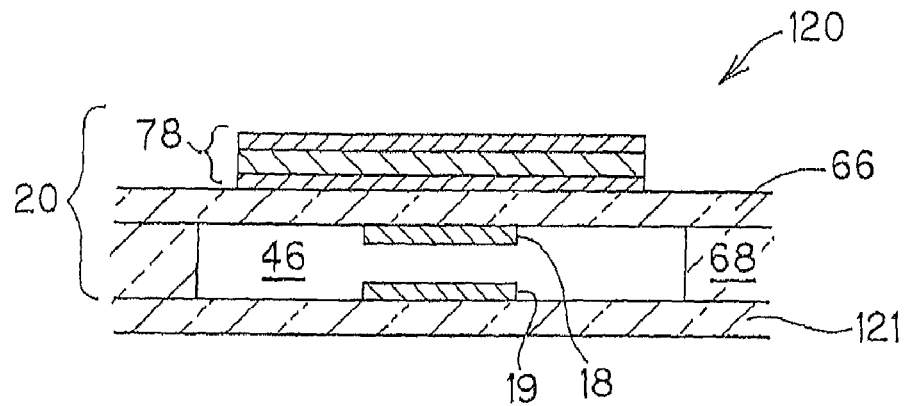
FIG. 6A is a cross-sectional view showing an example where a piezoelectric/electrostrictive actuator was applied as an actuator portion of a micro switch, showing a nonconductive state (off).
Figure 6B:
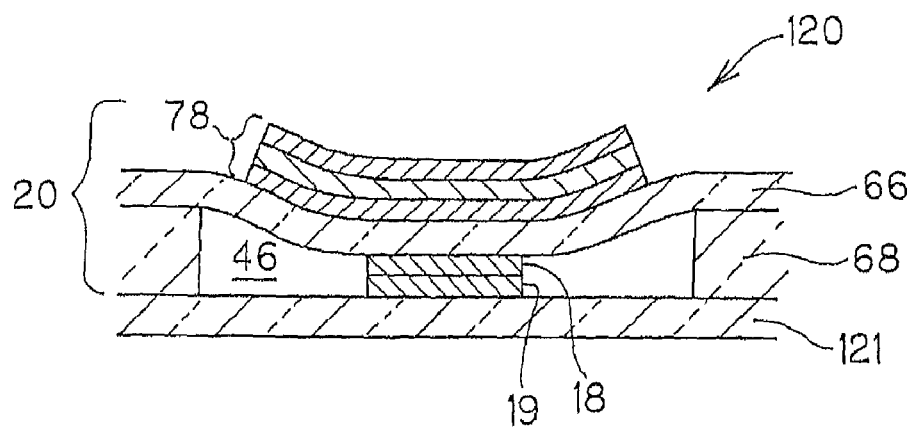
FIG. 6B is a cross-sectional view showing an example where a piezoelectric/electrostrictive actuator was applied as an actuator portion of a micro switch, showing a conductive state (on).

FIGS. 6A and 6B are cross-sectional views each showing an example where a piezoelectric/electrostrictive actuator is applied as an actuator portion for a micro switch. In the micro switch 120 shown in the figures, a switch electrode 18 is provided inside the cavity 46 of the piezoelectric/electrostrictive actuator 20, a terminal board 121 is provided so as to cover the cavity 46, and a switch electrode 19 is provided so as to face the switch electrode 18. When the vibration portion 66 is not transformed, the switches 18, 19 are nonconductive (off) (see FIG. 6A). However, when the piezoelectric/electrostrictive body 79 has a displacement to transform the vibration portion 66, the switches 18, 19 become conductive (ON) (see FIG. 6B).

Figure 7:
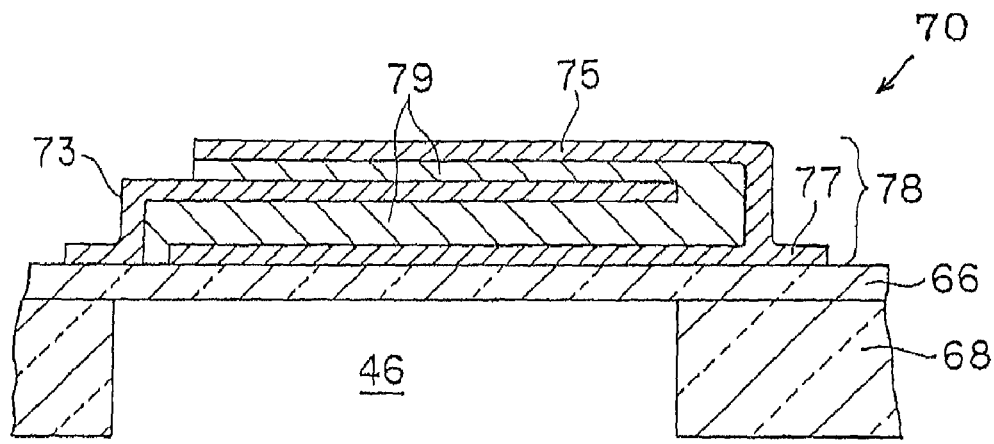
FIG. 7 is a cross-sectional view showing an example of the piezoelectric/electrostrictive actuator.
Figure 8:
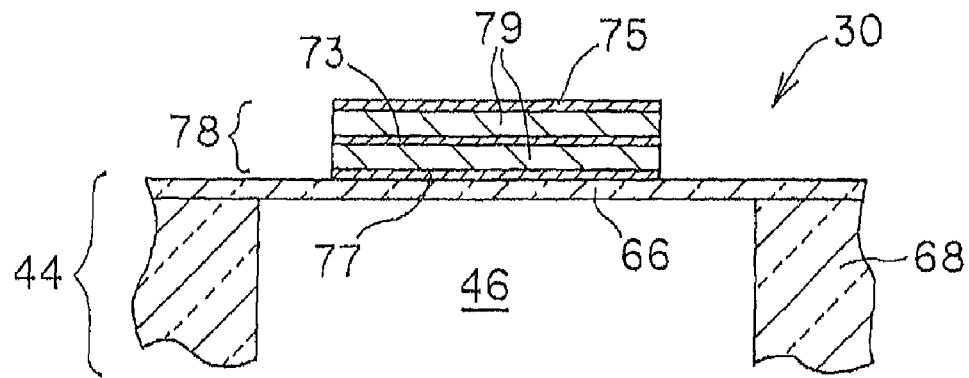
FIG. 8 is a cross-sectional view showing an example of the piezoelectric/electrostrictive actuator.
Figure 9:
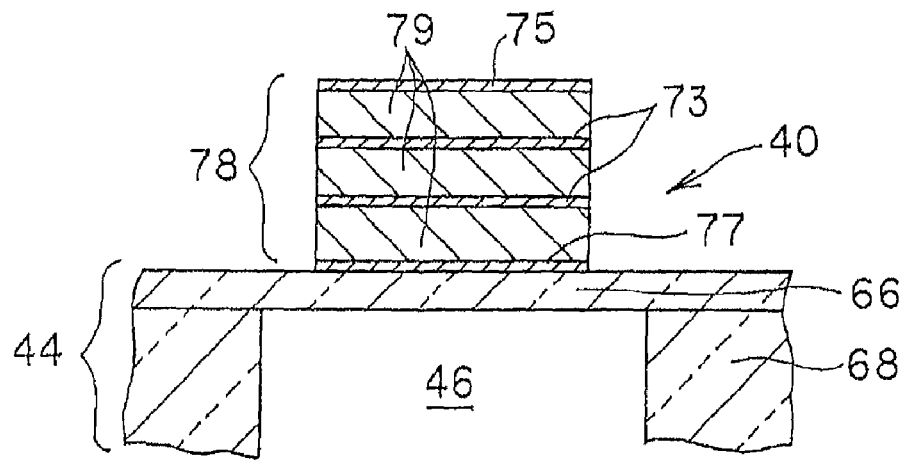
FIG. 9 is a cross-sectional view showing an example of the piezoelectric/electrostrictive actuator.

As piezoelectric/electrostrictive actuators, besides the piezoelectric/electrostrictive actuator 20 having one layer of the piezoelectric/electrostrictive body, piezoelectric/electrostrictive actuators 70, 30 and 40, whose cross sections are shown in FIGS. 7, 8 and 9, are shown as examples. FIG. 7 is a cross-sectional view showing a cross section according to FIG. 2. FIGS. 8 and 9 are cross-sectional views each showing a cross section according to FIG. 3. Each of the piezoelectric/electrostrictive actuators 70, 30 and 40 shown in FIGS. 7, 8 and 9 is in common with the piezoelectric/electrostrictive actuator 20 in that it has a substrate 44 and a piezoelectric/electrostrictive actuating portion 78 and that the substrate 44 is obtained by unitarily forming a thick support portion 68 having a cavity 46 and a vibration portion 66 covering the cavity 46. However, each of the piezoelectric/electrostrictive actuator 70 and the piezoelectric/electrostrictive actuator 30 (see FIGS. 7 and 8) is different from the piezoelectric/electrostrictive actuator 20 in that it has two layers of piezoelectric/electrostrictive bodies 79 sandwiched between the upper electrode 75 and intermediate electrode 73 and between the intermediate electrode 73 and the lower electrode 77. The piezoelectric/electrostrictive actuator 40 (see FIG. 9) is different from the piezoelectric/electrostrictive actuator 20 in that it has three layers of piezoelectric/electrostrictive bodies 79. In the present specification, for convenience sake, the electrode present nearest to the vibration portion of the piezoelectric/electrostrictive actuating portion is referred to as the lower electrode, the electrode present farthest from the vibration portion is referred to as the upper electrode, and the electrode other than the upper electrode and the lower electrode is referred to as an intermediate electrode in the case that a plurality of piezoelectric/electrostrictive bodies are laminated.

Next, with employing the case of the piezoelectric/electrostrictive actuator 20 as an example, a method for manufacturing a piezoelectric/electrostrictive actuator will be described. In the case of using a ceramic material for the substrate in manufacturing a piezoelectric/electrostrictive actuator, it can be manufactured by a green sheet lamination method, and the piezoelectric/electrostrictive actuating portion can be manufactured by a thin or thick film formation method.

The substrate 44 is manufactured as follows. For example, a binder, a solvent, a dispersant, a plasticizer, and the like are added to a ceramic powder of, for example, zirconium oxide, and they are mixed to prepare slurry. After the slurry is subjected to a defoaming treatment, a green sheet having a predetermined thickness is manufactured by a method such as a reverse roll coater method or a doctor blade method. Then, the green sheet is machined by a method such as punching using a die or laser processing into various shapes required. After a plurality of green sheets are piled up in sequence, a ceramic green laminate body is obtained by, for example, pressure bonding with heat. The green sheet laminate body obtained is fired at a temperature of about 1200 to 1600° C. to obtain the substrate 44.

Next, a piezoelectric/electrostrictive actuating portion 78 is formed on one surface of the substrate 44. For example, the lower electrode 77 is printed in a predetermined position on the surface of the substrate 44 by a membrane formation method such as screen printing, followed by firing at a temperature of about 1250 to 1450° C., and then the piezoelectric/electrostrictive body 79 is printed, followed by firing at a temperature of about 1100 to 1350° C., and then the upper electrode 75 is printed, followed by firing at a temperature of preferably 500° C. to 900° C. to form a piezoelectric/electrostrictive actuating portion 78. Then, an electrode lead for connecting the electrode to the driving circuit is printed, followed by firing. By selecting a suitable material, unitary firing at one time is also possible after each of the electrodes of the piezoelectric/electrostrictive actuating portion, the piezoelectric/electrostrictive body, and the electrode lead are printed sequentially.

After the piezoelectric/electrostrictive actuator 20 is formed as described above, when polarization is required for the piezoelectric/electrostrictive actuator 20, a polarization treatment is performed. Polarization is performed by, for example, applying a voltage (polarization voltage) sufficiently higher than the driving voltage expected to be used between the upper electrode 75 and the lower electrode 77. Though it is not limited, when the driving voltage is 30V, polarization is performed by setting the polarization voltage to be about 70V. Then, the piezoelectric/electrostrictive actuator 20 subjected to the polarization treatment is tested to confirm whether the substrate 44 and the piezoelectric/electrostrictive actuating portion 78 are normally manufactured or not. When the substrate 44 and the piezoelectric/electrostrictive actuating portion 78 are shifted from each other or when the vibration portion 66 has undulation, there is a case that a desired displacement amount cannot be obtained even the same (driving) voltage is applied between the electrodes.

An example of a piezoelectric/electrostrictive actuator has been described above. A piezoelectric/electrostrictive sensor targeted by a method and an apparatus for testing a piezoelectric/electrostrictive sensor of the present invention has only a difference in the electrode/mechanical conversion and the mechanical/electrode conversion, and the structure is similar to the aforementioned piezoelectric/electrostrictive actuator. Regarding the piezoelectric/electrostrictive sensor, the description with referring to a drawing is omitted.

Next, an apparatus for measuring the resonance frequency characteristic value, the displacement, and the capacitance will be described. The resonance frequency characteristic value and the capacitance are used to estimate the displacement in a method and an apparatus for testing a piezoelectric/electrostrictive actuator of the present invention.

Figure 10:
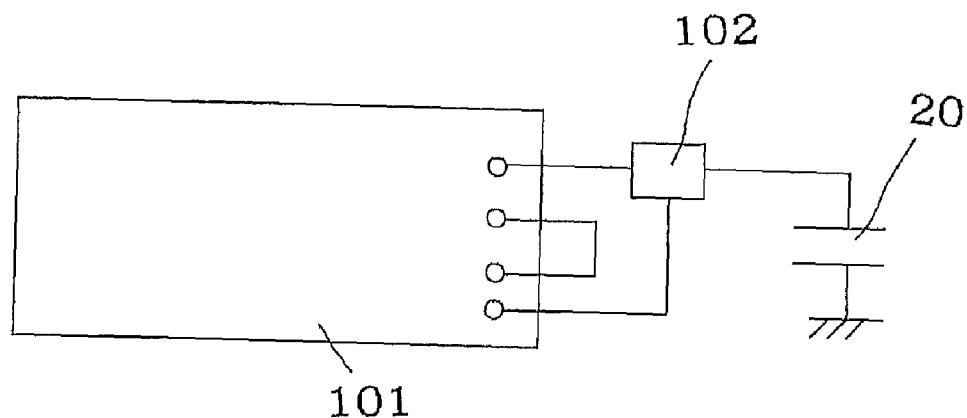
FIG. 10 is a configuration diagram showing an example of a resonance frequency characteristic value measurement apparatus.

FIG. 10 is a configuration diagram of an apparatus for measuring a resonance frequency characteristic value of a piezoelectric/electrostrictive actuator. The resonance frequency characteristic value of a piezoelectric/electrostrictive actuator can be measured by electrically connecting the network analyzer 101 to (for example) the piezoelectric/electrostrictive actuator 20 (see FIGS. 1 to 3) to be tested by means of the directional coupler 102 and the prove (measurement jig) to analyze a transmission wave or a reflection wave to the input signal (reflection method or the like), for example, by the conductance and susceptance.

Figure 11:
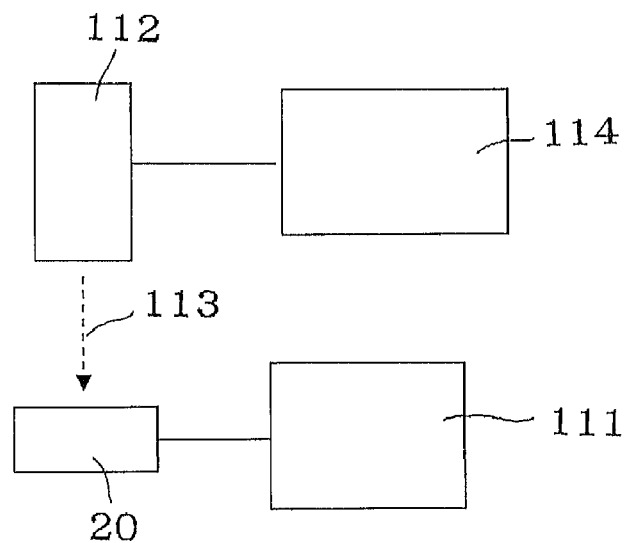
FIG. 11 is a configuration diagram showing an example of a displacement measurement apparatus.

FIG. 11 is a configuration diagram of an apparatus for measuring a displacement when a piezoelectric/electrostrictive actuator is driven. The displacement of the piezoelectric/electrostrictive actuator 20 can be measured by a waveform measurement analysis apparatus 114 by (for example) vibrating the piezoelectric/electrostrictive actuator 20 (see FIGS. 1 to 3) to be tested by a drive voltage signal output from the drive apparatus 111 having a signal generator and an electric power amplifier, irradiating the displacement measurement point in the piezoelectric/electrostrictive actuator 20 with a laser 113 output from the laser Doppler vibrometer 112, and inputting the vibration speed waveform obtained of the piezoelectric/electrostrictive actuator 20 into the waveform measurement analysis apparatus 114.

Figure 12:
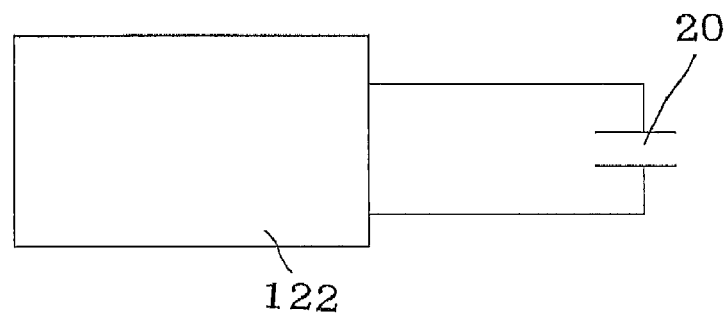
FIG. 12 is a configuration diagram showing an example of a frequency characteristic measurement system.

FIG. 12 is a configuration diagram showing a frequency characteristic measurement system for measuring the capacitance of a piezoelectric/electrostrictive actuator. As shown in FIG. 12, (for example) the capacitance of the piezoelectric/electrostrictive actuator 20 (see FIGS. 1 to 3) can be measured by a LCR meter 122. Specifically, the LCR meter 122 is electrically connected to the piezoelectric/electrostrictive actuator 20 by means of a probe (measurement jig) to measure the capacitance and the loss; of the piezoelectric/electrostrictive body 79 with applying a voltage between the upper electrode 75 and the lower electrode 77. By combining the capacitance, the loss, and the equivalent resistance (parallel, series) calculated from the capacitance and the loss, defects in the size (electrode area, thickness, electrode disconnection, etc.), polarization, insulation properties, output (displacement, sensitivity), and the like of the piezoelectric/electrostrictive device can be detected. The capacitance and equivalent resistance may be used in combination with the resonance frequency characteristic value or may be used alone for judgment. The voltage and the frequency applied for the capacitance and the loss are, for example, a frequency of 1 kHz and, for example, a voltage of about 1V. The measurement conditions are responded by using either the value where the circuit is regarded as a circuit where the capacity and the resistance are connected in parallel or the value where they are connected in series according to the kind of the defect.

The apparatus for measuring the resonance frequency characteristic value, the displacement and the capacitance of the aforementioned piezoelectric/electrostrictive actuator can be used for a piezoelectric/electrostrictive sensor.

Next, regarding a method and an apparatus for testing a piezoelectric/electrostrictive actuator of the present invention, a specific method for estimating the displacement will be described based on the actual measurement data.

Figure 13:
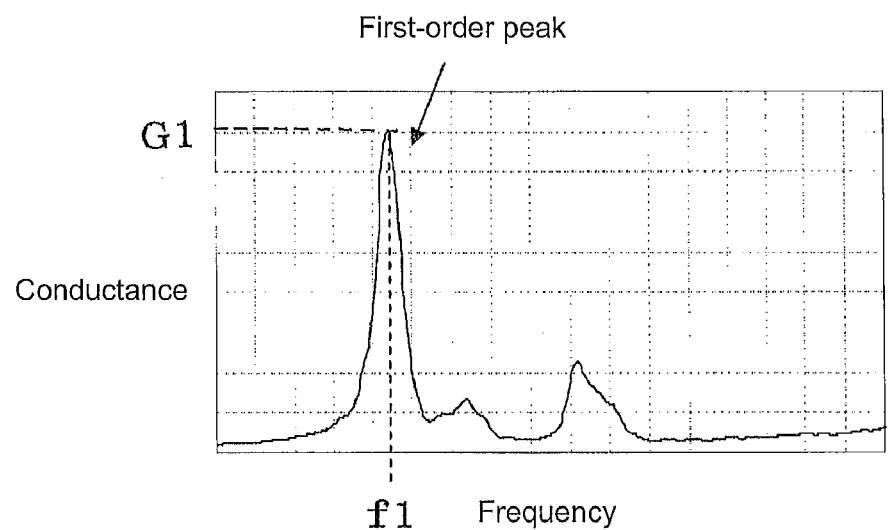
FIG. 13 is a graph showing an example of a frequency characteristic of a piezoelectric/electrostrictive actuator.

FIG. 13 is a graph showing an example of the frequency characteristics of the piezoelectric/electrostrictive actuator 20 measured by the use of an apparatus described above and shown in FIG. 10 and showing the frequency characteristics of a conductance shown in the screen of a network analyzer. From the frequency characteristics shown in FIG. 13, the first order peak conductance value (G1) and resonance frequency (f1) are obtained. The conductance value (G1) corresponds with the peak height of the resonance waveform of the resonance frequency characteristic value of the first order, and the resonance frequency (f1) corresponds with the first order (k=1) of the first order resonance frequency.

By the aforementioned conductance value (G1) and the resonance frequency (f1), the estimated displacement standard value MV is given as the following formula (11). The formula (11) is a formula obtained from the formula (2) with R1=G1 and k=3. Depending on whether the estimated displacement is in a certain range (quality control value) or not, it is possible to test the quality of the piezoelectric/electrostrictive actuator.

$$\text{Estimated displacement standard value } MV = G1/f1^3 \tag{11}$$

Figure 14:
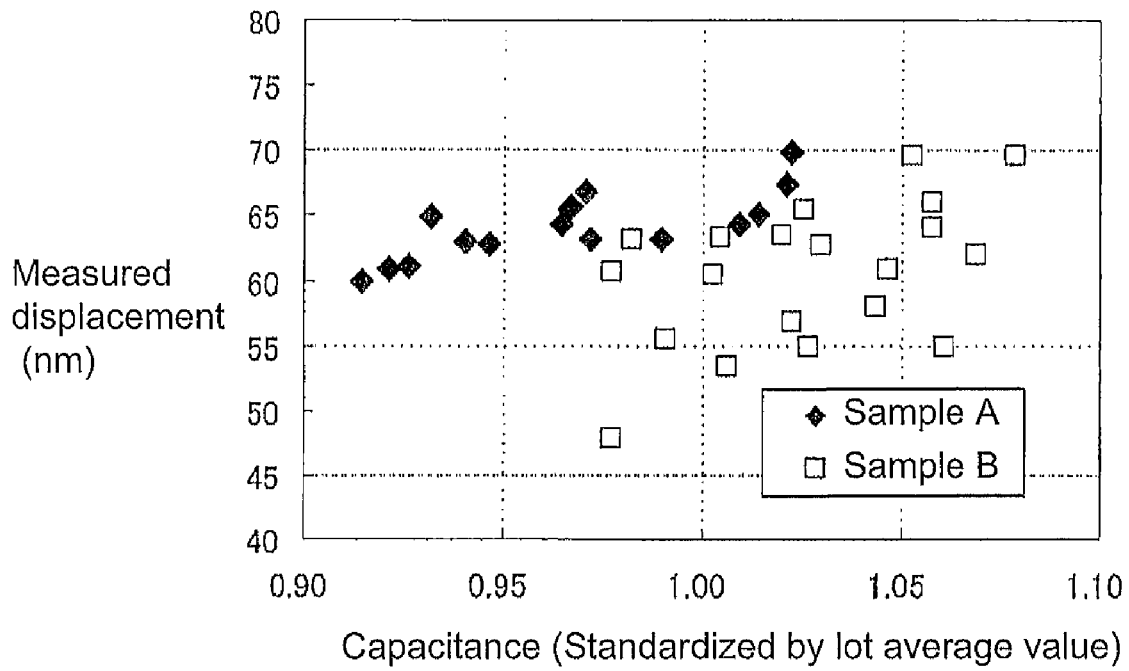
FIG. 14 is a graph showing a relation between the measured displacement and the capacitance of a piezoelectric/electrostrictive actuator.
Figure 15:
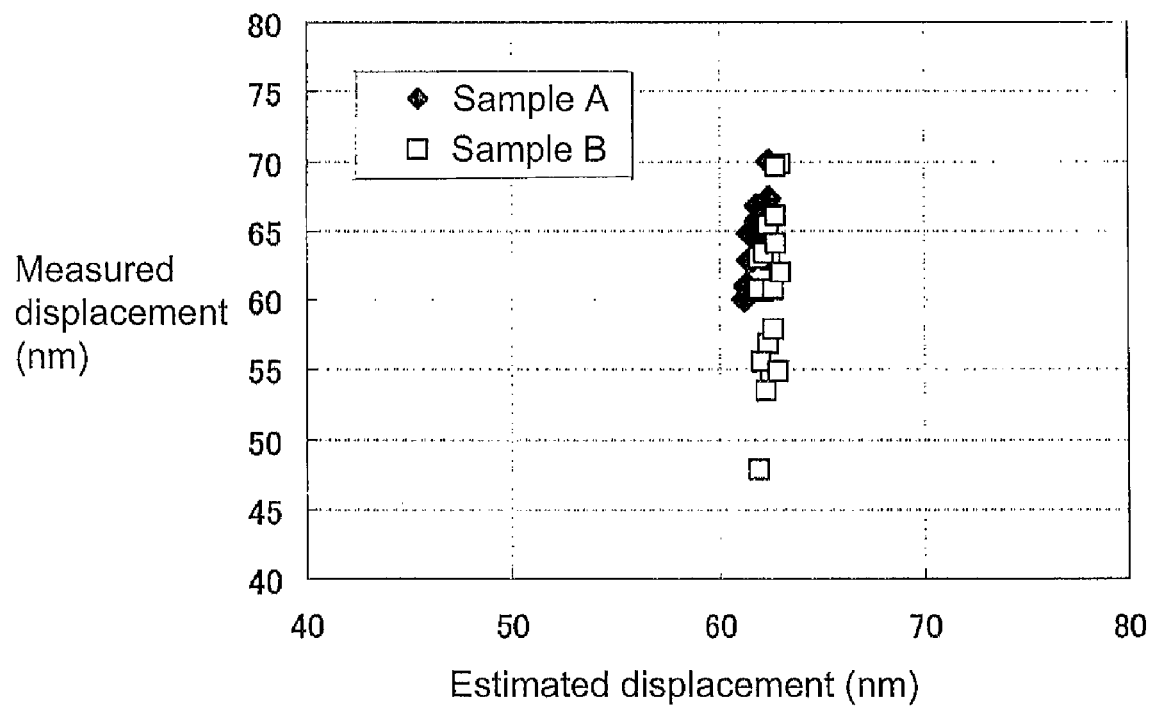
FIG. 15 is a graph showing the estimated displacement and the measured displacement of a piezoelectric/electrostrictive actuator.

FIG. 14 is a graph showing the relation between the measured displacement and the capacitance (value standardized by a lot average value) as the sample A and sample B extracted from the same lot among the manufactured piezoelectric/electrostrictive actuators 20 as the objects. In addition, FIG. 15 is a graph obtained by setting up the first order regression equation of the measured displacement and the capacitance with the sample A and sample B as the objects without distinction and showing the relation between the estimated displacement and the measured displacement. Incidentally, the sample A is a sample having a small position shift amount between the substrate 44 and the piezoelectric/electrostrictive actuating portion 78 and a small undulation of the vibration portion 66, and the sample B is a sample having a large position shift amount between the substrate 44 and the piezoelectric/electrostrictive actuating portion 78 and a large undulation of the vibration portion 66.

From the results shown in FIGS. 14 and 15, it is understood that, when the position shift between the substrate 44 and the piezoelectric/electrostrictive actuating portion 78 and the undulation amount of the vibration portion 66 in the piezoelectric/electrostrictive actuator 20 are changed, correlation between the displacement and the capacity becomes poor to fail to estimate the displacement by the capacitance.

Figure 16:
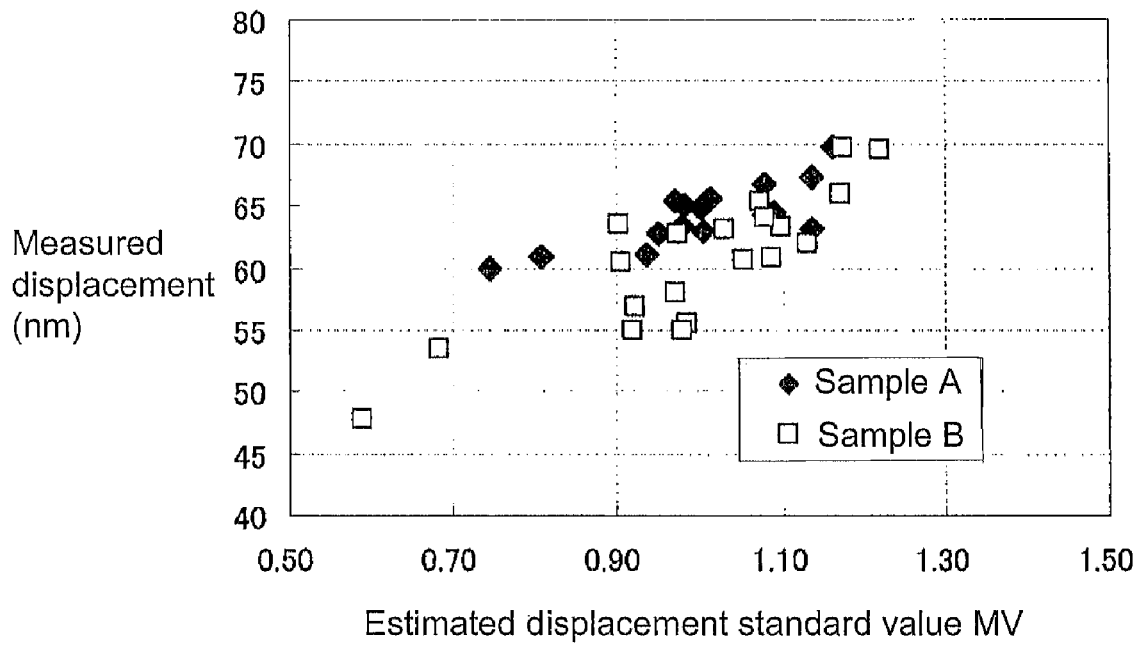
FIG. 16 is a graph showing the relation between the displacement and the estimated displacement standard value MV of a piezoelectric/electrostrictive actuator.
Figure 17:
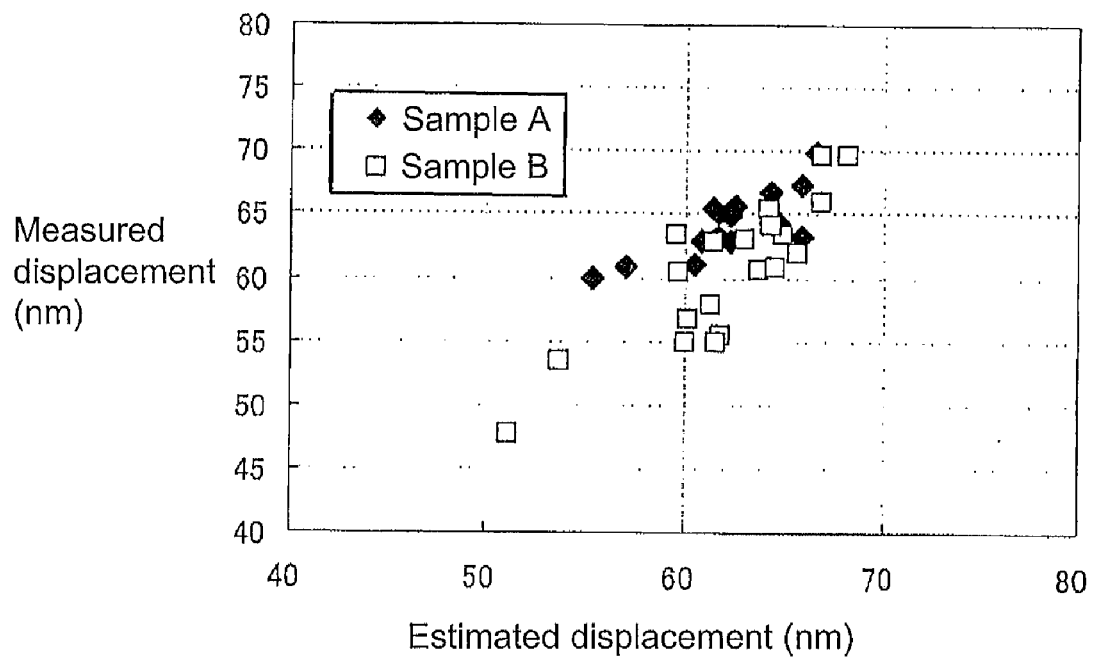
FIG. 17 is a graph showing the relation between the estimated displacement and the measured displacement of a piezoelectric/electrostrictive actuator.

FIG. 16 is a graph showing the relation of the displacement and the estimated displacement amount standard value MV (standardized by a lot average value) with the same sample A and sample B as the objects. FIG. 17 is a graph obtained by setting up the first order regression equation of the measured displacement with the same sample A and sample B as the objects without distinction and showing the relation between the estimated displacement and the measured displacement.

From the results shown in FIGS. 16 and 17, it is understood that, even when the position shift between the substrate 44 and the piezoelectric/electrostrictive actuating portion 78 and the undulation amount of the vibration portion 66 in the piezoelectric/electrostrictive actuator 20 are changed, correlation between the displacement and the estimated displacement standard value MV is secured to be able to estimate the displacement with high precision.

Since a piezoelectric/electrostrictive actuator has conventionally been tested on the basis of only the capacitance of the piezoelectric/electrostrictive body, the difference of the other elements constituting the piezoelectric/electrostrictive actuator, that is, the difference of the substrate and the like constituted of the vibration portion and the support portion among the products has not been reflected on the test result. Therefore, it had a limitation in improvement of the precision of the test. However, in a method and an apparatus for testing a piezoelectric/electrostrictive actuator of the present invention, the test is performed on the basis of a resonance frequency characteristic value obtained from the manufactured piezoelectric/electrostrictive actuator. Since all the elements (including unpredictable elements) constituting the piezoelectric/electrostrictive actuator are reflected on the resonance frequency characteristic value, the variance in the displacement can be identified without fail, and the precision for the test is higher than that by a conventional means to be able to judge whether it is a good product or not more precisely. Since the test is not accompanied by any disassembly/breakage of a piezoelectric/electrostrictive actuator, the test does not require much time. For example, a micro switch where a good piezoelectric/electrostrictive actuator which passed the test is used as the actuator portion has the displacement of the vibration portion in a certain range and the suppressed variance of switch operation.

A method and an apparatus for testing a piezoelectric/electrostrictive actuator of the present invention have been described with showing an example of a method for estimating a displacement. Since a method and an apparatus for testing a piezoelectric/electrostrictive sensor of the present invention is an invention in accordance with a method and an apparatus for testing a piezoelectric/electrostrictive actuator of the present invention, the description with referring to a drawing will be omitted.

An apparatus for testing a piezoelectric/electrostrictive actuator of the present invention and an apparatus for testing a piezoelectric/electrostrictive sensor can be manufactured by purchasing a commercial network analyzer or impedance analyzer, creating a program (software) for realizing the aforementioned means, and mount it on a computer. The input required by an apparatus for testing a piezoelectric/electrostrictive actuator of the present invention and an apparatus for testing a piezoelectric/electrostrictive sensor of the present invention can be obtained by the network analyzer and the impedance analyzer. The input is one or more frequency characteristic values selected from the group consisting of the heights and areas of the peaks of the resonance waveforms and the difference of the maximum and minimum of the first order or first to higher orders of the resonance frequency characteristic values and the k-th order (k=1 to 4) of the first or first to higher orders of resonance frequencies. By an apparatus for testing a piezoelectric/electrostrictive actuator of the present invention and an apparatus for testing a piezoelectric/electrostrictive sensor, a method for testing a piezoelectric/electrostrictive actuator of the present invention and a method for testing a piezoelectric/electrostrictive sensor can be conducted.

Piezoelectric/electrostrictive devices (piezoelectric/electrostrictive actuator and piezoelectric/electrostrictive sensor) which are the targets of a method and an apparatus for testing a piezoelectric/electrostrictive device of the invention each shows a unit having a comprehensive function by the use of strain induced by an electric field or charge/electric field induced by stress and has a piezoelectric/electrostrictive body and at least a pair of electrodes as the constituents, and it is not limited to a narrowly-defined piezoelectric/electrostrictive device using an inverse piezoelectric effect generating a strain amount almost proportional to the applied electric field, a piezoelectric effect generating an amount of charge induced by stress, or an electrostrictive effect generating a strain amount almost proportional to the square of the applied electric field, and there are included piezoelectric/electrostrictive devices each uses a phenomenon such as polarization inversion shown in the general ferroelectric material and phase transition between an antiferroelectric phase and a ferroelectric phase shown in an antiferroelectric material. In addition, whether a polarization treatment is performed or not is suitably determined on the basis of the characteristics of the material used for the piezoelectric/electrostrictive body constituting a piezoelectric/electrostrictive device.

Next, an embodiment of a method for adjusting a piezoelectric/electrostrictive actuator of the present invention will be described. In a method for adjusting a piezoelectric/electrostrictive actuator of the present invention, the displacement of a plurality of piezoelectric/electrostrictive actuators is estimated by the use of the aforementioned method for testing a piezoelectric/electrostrictive actuator of the present invention, and an upper electrode is trimmed with regard to at least some of the plurality of piezoelectric/electrostrictive actuators on the basis of the estimated displacement of each piezoelectric/electrostrictive actuator to adjust the displacement of the piezoelectric/electrostrictive actuators uniformly. Here, trimming means to remove an unnecessary portion and to remove a part of a specific portion of a piezoelectric/electrostrictive actuator in order to adjust the displacement of the piezoelectric/electrostrictive actuator.

Since the resonance frequency characteristic value R in the formula (1) is changed by trimming the upper electrode of the piezoelectric/electrostrictive actuator, the displacement of the piezoelectric/electrostrictive actuator can be adjusted. In addition, to trim the upper electrode of a piezoelectric/electrostrictive actuator means to change the conductance G1 in the formula (11).

When the upper electrode is trimmed, the aforementioned resonance frequency characteristic value R (conductance G1) becomes small. Therefore, it is preferable that the displacement of a plurality of piezoelectric/electrostrictive actuators is estimated and that the upper electrode is trimmed with regard to the piezoelectric/electrostrictive actuator having the estimated displacement larger than the standard value of the displacement set in advance. In addition, it is preferable that the relation between the displacement of the piezoelectric/electrostrictive actuator to be changed and the trimming amount of the upper electrode is measured in advance to prepare a standard curve and that the trimming amount is determined on the basis of the measurement result (standard curve).

The trimming method of the upper electrode of the piezoelectric/electrostrictive actuator is preferably a processing method such as laser irradiation, electron beam irradiation, and cutting. Of these, the processing method by laser irradiation is more preferable because a beam wave length can be selected in accordance with the characteristics of the material to be removed. In laser irradiation, it is particularly preferable to use a YAG laser of the third or fourth order. The wave length of the laser is close to the wave length absorption band of gold (Au) capable of forming the upper electrode, it is easy to narrow down the beam, and depth of field is small. Therefore, even in the case of a thin upper electrode, trimming is possible without imparting a damage such as a crack on the piezoelectric/electrostrictive body.

Figure 18A:
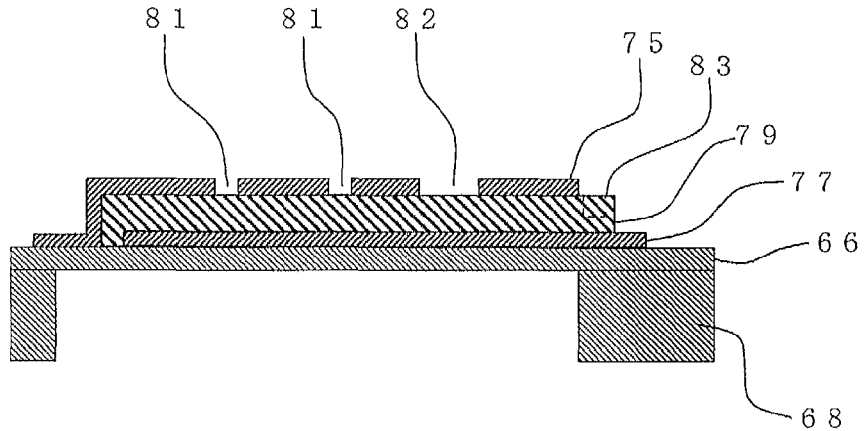
FIG. 18A is a schematic view showing a cross section including the vibration portion and the piezoelectric/electrostrictive actuating portion of a piezoelectric/electrostrictive actuator of the present invention adjusted according to a method for adjusting a piezoelectric/electrostrictive actuator of the present invention.
Figure 18B:
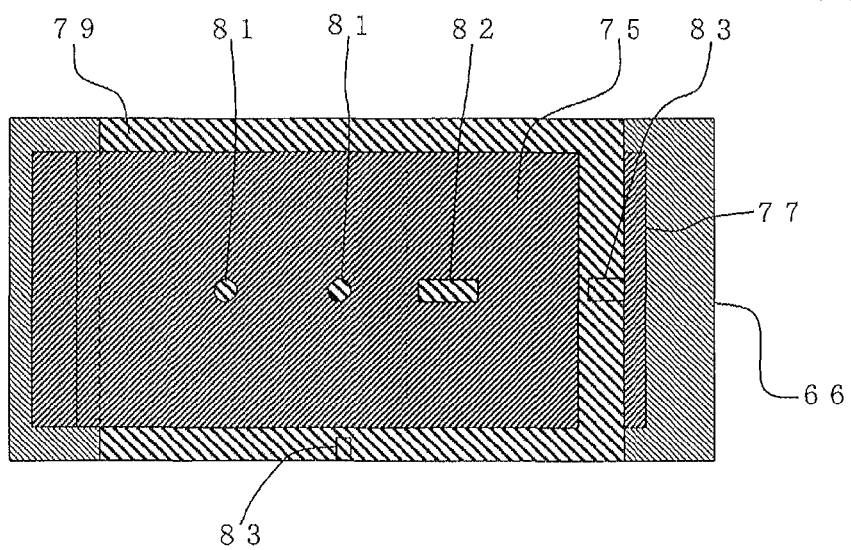
FIG. 18B is a plan view schematically showing a piezoelectric/electrostrictive actuator of the present invention according to the present invention adjusted by a method for adjusting a piezoelectric/electrostrictive actuator of the present invention.

In addition, as shown in FIGS. 18A and 18B, it is preferable that the trimming of the upper electrode 75 of the piezoelectric/electrostrictive actuator 50 is performed by forming a circular through-hole 81 or a slit (slit in the upper electrode) 82 in the upper electrode 75. The circular through-hole 81 is a through-hole having a diameter of 10 to 50 μm formed in the upper electrode 75, and at least one through-hole is formed in accordance with the displacement to be adjusted. The circular through-hole 81 is preferably formed in the central portion of the upper electrode 75 because the displacement is remarkably changed. The slit 82 to be formed in the upper electrode 75 is a rectangular through-hole, and at least one slit is formed in accordance with the displacement to be adjusted. Both the slit 82 and the circular through-hole 81 may be formed. The width of the slit 82 is preferably 10 to 50 μm. The slit is preferably formed in the upper electrode in the case that more remarkable change of the displacement of the piezoelectric/electrostrictive actuator is desired. FIG. 18A is a schematic view showing a cross section including the vibration portion and the piezoelectric/electrostrictive actuating portion of a piezoelectric/electrostrictive actuator of the present invention adjusted according to a method for adjusting a piezoelectric/electrostrictive actuator of the present invention. FIG. 18B is a plan view schematically showing a piezoelectric/electrostrictive actuator of the present invention according to the present invention adjusted by a method for adjusting a piezoelectric/electrostrictive actuator of the present invention.

Figure 20:
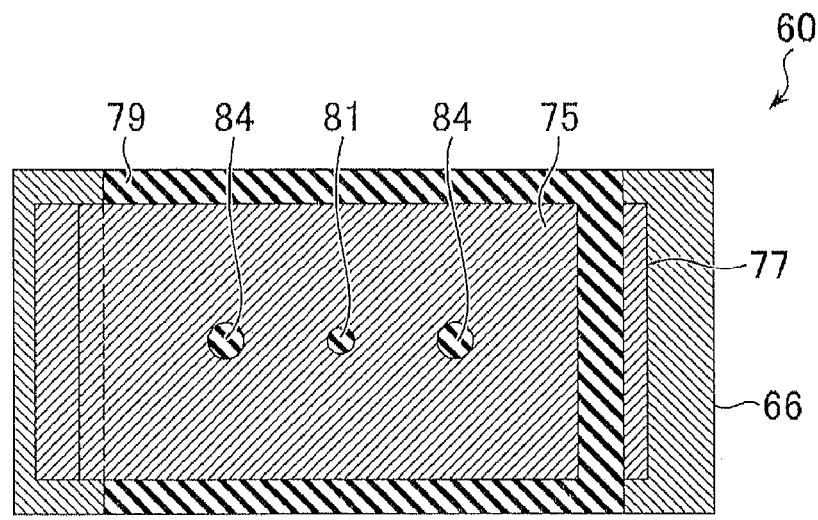
FIG. 20 is a plan view schematically showing a piezoelectric/electrostrictive actuator of the present invention adjusted by a method for adjusting a piezoelectric/electrostrictive actuator of the present invention.
Figure 21:
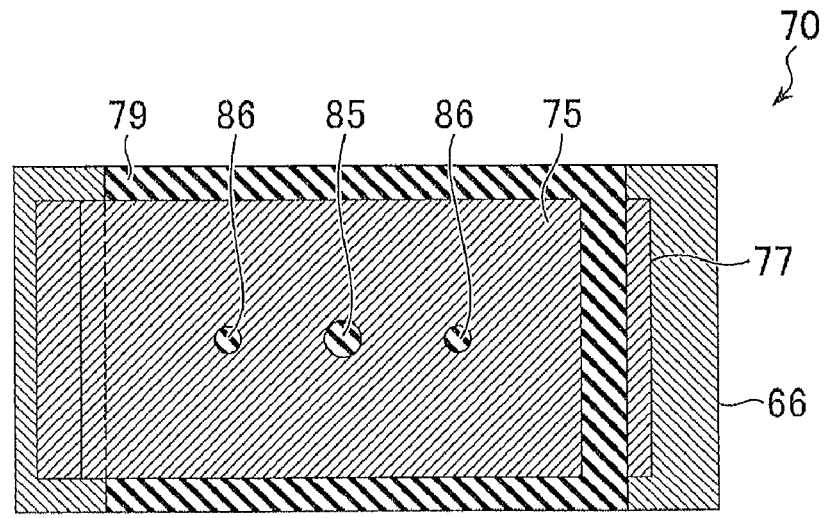
FIG. 21 is a plan view schematically showing a piezoelectric/electrostrictive actuator of the present invention adjusted by a method for adjusting a piezoelectric/electrostrictive actuator of the present invention.

Further, as in the piezoelectric/electrostrictive actuator 60 shown in FIG. 20, in the case that the trimming of the upper electrode 75 is circular through-holes 81 and 84, it is preferable that the through-holes 81 and 84 have different diameters. In the piezoelectric/electrostrictive actuator 70 shown in FIG. 21, in the case that the trimming of the upper electrode 75 is circular through-holes 85 and 86 likewise, the through-holes 85 and 86 have different diameters, which is a preferable embodiment.

Figure 22:
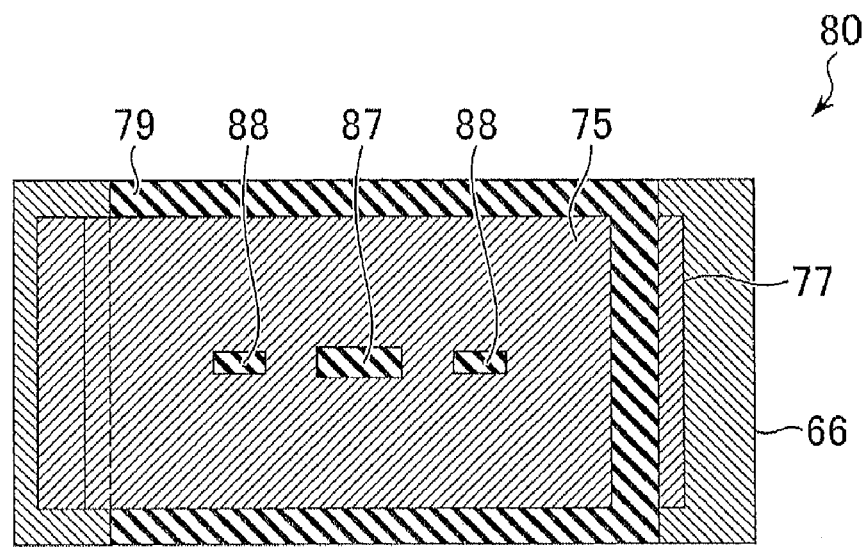
FIG. 22 is a plan view schematically showing a piezoelectric/electrostrictive actuator of the present invention adjusted by a method for adjusting a piezoelectric/electrostrictive actuator of the present invention.
Figure 23:
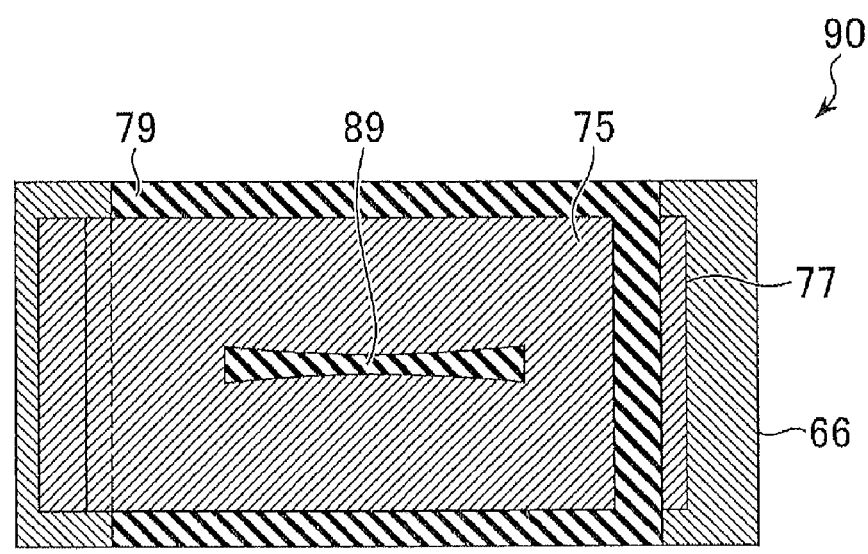
FIG. 23 is a plan view schematically showing a piezoelectric/electrostrictive actuator of the present invention adjusted by a method for adjusting a piezoelectric/electrostrictive actuator of the present invention.

In addition, as the piezoelectric/electrostrictive actuator 80 shown in FIG. 22, in the case that the trimming of the upper electrode 75 is slits 87 and 88, it is preferable that the slits 87 and 88 have different widths. As the piezoelectric/electrostrictive actuator 90 shown in FIG. 23, in the case that the trimming of the upper electrode 75 is one slit 89, the width of the slit may be changed (different) in such a manner that (for example) the end portions are wider.

Figure 19A:
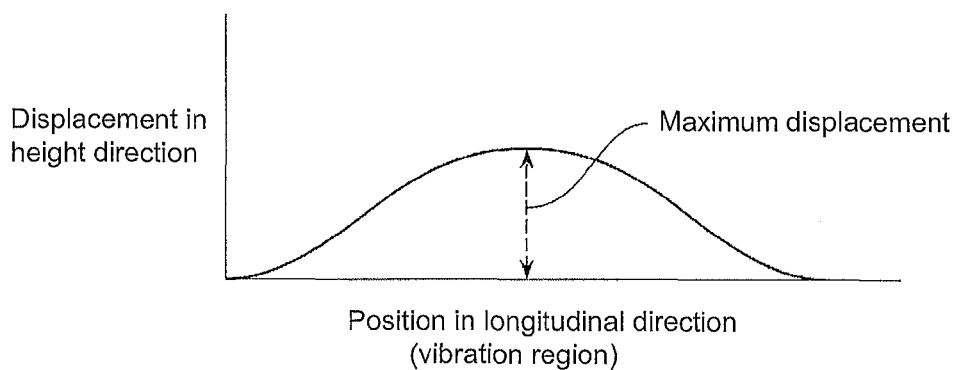
FIG. 19A is a graph showing a displacement in each position in the longitudinal direction of a piezoelectric/electrostrictive actuator.
Figure 19B:
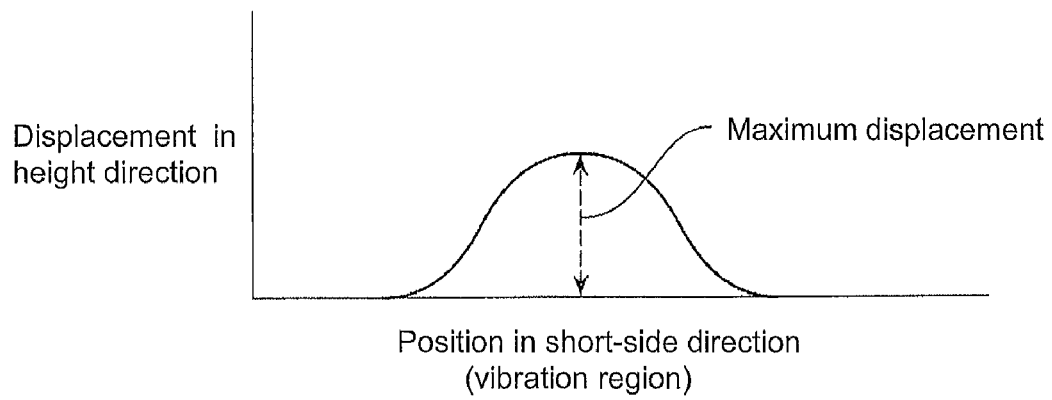
FIG. 19B is a graph showing a displacement in each position in the short-side direction of a piezoelectric/electrostrictive actuator.

A preferable position of trimming of a piezoelectric/electrostrictive actuator (place to be trimmed) is the portion where the maximum displacement of the piezoelectric/electrostrictive actuator is generated. FIG. 19A is a graph showing a displacement in each position in the longitudinal direction of a piezoelectric/electrostrictive actuator. The longitudinal e direction means the direction shown in FIG. 2 (direction of the A-A' cross section in FIG. 1) in the piezoelectric/electrostrictive actuator 20 shown in FIGS. 1 to 3. In addition, FIG. 19B is a graph showing a displacement in each position in the short-side direction of a piezoelectric/electrostrictive actuator, and the direction is the direction shown in FIG. 3 (direction of the B-B' cross section in FIG. 1) in the piezoelectric/electrostrictive actuator 20 shown in FIGS. 1 to 3. As understandable from FIGS. 19A, 19B, 2 and 3, in the piezoelectric/electrostrictive actuator 20, the portion where the maximum displacement is generated is the central portion of the piezoelectric/electrostrictive actuator (with the cavity as the base), and the piezoelectric/electrostrictive actuators 50, 60, 70, 80 and 90 shown in FIGS. 18A to 23 are trimmed in preferable positions.

In addition, the preferable position of trimming of the piezoelectric/electrostrictive actuator (place to be trimmed) is the portion having the maximum amplitude in the first order of the resonance mode. In the piezoelectric/electrostrictive actuator 20, the portion having the maximum amplitude of the resonance made of the first order is the central portion of the piezoelectric/electrostrictive actuator (with the cavity as the base), and the piezoelectric/electrostrictive actuators 50, 60, 70, 80 and 90 shown in FIGS. 18A to 23 are trimmed in preferable positions.

The plurality of piezoelectric/electrostrictive actuators where the displacement is adjusted by a method for adjusting a piezoelectric/electrostrictive actuator of the present invention may be piezoelectric/electrostrictive actuators assembled on one substrate or present separately on different substrates.

In addition, it is also a preferable embodiment where the "piezoelectric/electrostrictive body" of each of at least part of the plurality of piezoelectric/electrostrictive actuators is trimmed on the basis of the estimated displacement of each of the piezoelectric/electrostrictive actuators to adjust the displacement of the plurality of piezoelectric/electrostrictive actuators uniformly.

When the piezoelectric/electrostrictive body is trimmed, the resonance frequency f in the formula (1) becomes small. Therefore, it is preferable that the displacement of the plurality of piezoelectric/electrostrictive actuators is estimated to subject the piezoelectric/electrostrictive body of each of the piezoelectric/electrostrictive actuators each having a displacement smaller than the standard value of the preset displacement to trimming. In addition, it is preferable that the relation between the displacement to be changed of the piezoelectric/electrostrictive actuator and the trimming amount of the piezoelectric/electrostrictive body is measured in advance to prepare a standard curve and that the trimming amount is determined on the basis of the measurement result (standard curve).

The trimming method of the piezoelectric/electrostrictive body of the piezoelectric/electrostrictive actuator is preferably a processing method such as laser irradiation, electron beam irradiation, and cutting. Of these, the processing method by laser irradiation is more preferable because a beam wave length can be selected in accordance with the characteristics of the material to be removed.

In addition, it is preferable that the trimming of the piezoelectric/electrostrictive body of the piezoelectric/electrostrictive actuator is performed by forming a slit in the piezoelectric/electrostrictive body. The slit formed in the piezoelectric/electrostrictive body is a rectangular groove, and at least one slit is formed in accordance with the displacement to be adjusted. The width of the slit is preferably 10 to 50 µm. The position for forming the slit is preferably an outer edge portion of the piezoelectric/electrostrictive body.

In addition, it is also a preferable embodiment where both the piezoelectric/electrostrictive body and the upper electrode of each of at least part of the plurality of piezoelectric/electrostrictive actuators are subjected to trimming. The piezoelectric/electrostrictive actuator shown in FIGS. 18A and 18B is an example where both the piezoelectric/electrostrictive body 79 and the upper electrode 75 were subjected to trimming. The trimming of the piezoelectric/electrostrictive body 79 was performed by forming the slit (slit of piezoelectric/electrostrictive body) 83.

Next, an embodiment of a piezoelectric/electrostrictive actuator of the present invention will be described. The piezoelectric/electrostrictive actuators 50, 60, 70, 80 and 90 shown in FIGS. 18A to 23 were obtained by adjusting the displacement uniformly by the use of a method for adjusting a piezoelectric/electrostrictive actuator of the present invention. Therefore, the piezoelectric/electrostrictive actuator 50, 60, 70, 80 and 90 were obtained by adjusting the displacement uniformly by the use of the aforementioned method for adjusting a piezoelectric/electrostrictive actuator of the present invention with regard to the piezoelectric/electrostrictive actuators before adjustment manufactured by the aforementioned method for manufacturing the piezoelectric/electrostrictive actuator 20 (see FIGS. 1 to 3).

Since the piezoelectric/electrostrictive actuators 50, 60, 70, 80 and 90 were obtained by adjusting the displacement uniformly by the use of the aforementioned method for adjusting a piezoelectric/electrostrictive actuator of the present invention, the displacement is uniform as a whole.

In a method for adjusting a piezoelectric/electrostrictive sensor of the present invention, the piezoelectric/electrostrictive actuator is replaced with a piezoelectric/electrostrictive sensor in the aforementioned method for adjusting a piezoelectric/electrostrictive actuator of the present invention. In a method for adjusting a piezoelectric/electrostrictive sensor of the present invention, by trimming a piezoelectric/electrostrictive sensor, the detection sensitivity can be adjusted efficiently. In addition, since a piezoelectric/electrostrictive sensor of the present invention has detection sensitivity adjusted by a method for adjusting a piezoelectric/electrostrictive sensor of the present invention, the detection sensitivity of a plurality of piezoelectric/electrostrictive sensors is adjusted uniformly.

EXAMPLE

Hereinbelow, the present invention will be described more specifically with referring to Examples. However, the present invention is by no means limited by these Examples.

Example 1

There was manufactured, as a piezoelectric/electrostrictive actuator before adjustment, a piezoelectric/electrostrictive actuator having the same structure as that of the piezoelectric/electrostrictive actuator 20 shown in FIGS. 1 to 3. The piezoelectric/electrostrictive actuator before adjustment was manufactured by the following method. In the first place, a binder, a solvent, a dispersant, and a plasticizer were mixed with zirconium oxide to prepare slurry. Next, the slurry was subjected to a defoaming treatment to manufacture a green sheet having a predetermined thickness by a reverse roll coater method. Then, the green sheet was processed by laser processing into a predetermined shape. After a plurality of green sheets were piled up in sequence, a ceramic green laminate body was obtained by pressure bonding with heat. The green sheet laminate body obtained was fired at a temperature of 1200 to 1600° C. to obtain the substrate (corresponding with the substrate 44 of FIGS. 2 and 3).

On one surface of the substrate, a piezoelectric/electrostrictive actuating portion (corresponding with the piezoelectric/electrostrictive actuating portion 78 of FIGS. 1 to 3) was formed. Specifically, the piezoelectric/electrostrictive actuator before adjustment was obtained by printing the lower electrode in a predetermined portion of one surface of the substrate by screen printing, followed by firing at 1250 to 1450° C., then printing a piezoelectric/electrostrictive body by screen printing, followed by firing at 1100 to 1350° C., and then printing the upper electrode by screen printing, followed by firing 500 to 900° C. to form a piezoelectric/electrostrictive actuating portion. Then, by the above method, two piezoelectric/electrostrictive actuators before adjustment was manufactured.

The piezoelectric/electrostrictive actuators before adjustment obtained above each had a thickness of the upper electrode of 0.5 μm, a thickness of the piezoelectric/electrostrictive body of 13 μm, a thickness of the lower electrode of 3 μm, and a thickness of a vibration portion of 10 μm (see WO2004/013918).

Next, the displacement of two piezoelectric/electrostrictive actuators before adjustment obtained above was adjusted to obtain two piezoelectric/electrostrictive actuators (Example 1). The adjustment of the displacement of the piezoelectric/electrostrictive actuators was performed by the following method. In the first place, the conductance value (G1) and the resonance frequency (f1) were obtained by the use of a network analyzer (trade name: E-5100A, produced by Agilent Technologies Japan Ltd.). Then, by the use of the aforementioned formula (11) ($MV = G1/f1^3$), the estimated displacement standard value MV of each of the piezoelectric/electrostrictive actuators before adjustment was obtained. Next, by the use of the standard curve (standard curve of the trimming amount) obtained by the method described below, the trimming amount of the upper electrode of each of the piezoelectric/electrostrictive actuators before adjustment was calculated out, and the upper electrode of each of the piezoelectric/electrostrictive actuators before adjustment was subjected to trimming to adjust the displacement of the two piezoelectric/electrostrictive actuators uniformly. The displacement of the two piezoelectric/electrostrictive actuators was adjusted in such a manner that the difference in the displacement between the two piezoelectric/electrostrictive actuators is within 1% (±0.5%). The trimming of the upper electrode was performed by forming a plurality of through-holes each having a diameter of 10 μm in the upper electrode by laser irradiation. Next, the estimated displacement standard value MV was obtained with regard to the piezoelectric/electrostrictive actuators after trimming was performed. The results of comparison of the displacement (estimated displacement) of the two piezoelectric/electrostrictive actuators between before trimming and after trimming are shown in Table 1. In the Table 1, "before processing" shows the estimated displacement of 24 piezoelectric/electrostrictive actuators before being subjected to trimming, and "after processing" shows the estimated displacement of two piezoelectric/electrostrictive actuators after being subjected to trimming. In addition, the trimming was performed on the piezoelectric/electrostrictive actuator of the "actuator No. 2".

TABLE 1

| Actuator No. | Displacement before processing | Displacement after processing |
| --- | --- | --- |
| 1 | 1.00 | 1.00 |
| 2 | 1.05 | 1.01 |

[Standard curve of trimming] The standard curve (relation between the removed area of the upper electrode and the change rate of the estimated displacement standard value MV) of the trimming amount was prepared by the following method. In the first place, a piezoelectric/electrostrictive actuator having the same shape as the piezoelectric/electrostrictive actuator before adjustment was manufactured, and the estimated displacement standard value of the piezoelectric/electrostrictive actuator was measured. Then, the upper electrode was subjected to trimming of a predetermined area, and the estimated displacement standard value of the piezoelectric/electrostrictive actuator after trimming was measured. Then, the estimated displacement standard value of a piezoelectric/electrostrictive actuator was measured with increasing the trimming area in stages to obtain the relation between the removed area of the upper electrode and the estimated displacement standard value change rate. Here, the estimated displacement standard value change rate is a rate based on the estimated displacement standard value of the piezoelectric/electrostrictive actuator in a state without trimming. Table 2 shows the relation between the estimated displacement standard value obtained above and the removed area of the upper electrode. From Table 2, the relation of the removal area of the upper electrode and the change rate of the estimated displacement standard value can be figured out.

TABLE 2

| Removed area of upper electrode | Estimated displacement standard value of change rate |
| --- | --- |
| 0.1% | −1% |
| 0.3% | −2% |
| 1.0% | −4% |

From Table 1, it can be understood that, by the aforementioned method for adjusting (the displacement of) the piezoelectric/electrostrictive actuator, the difference of the displacement of the piezoelectric/electrostrictive actuator was reduced to 1% after the adjustment (after trimming) to be uniformalized while it was 5% before the adjustment (before trimming).

INDUSTRIAL APPLICABILITY

A method and an apparatus for testing a piezoelectric/electrostrictive actuator of the present invention can suitably be used as a means for testing various piezoelectric/electrostrictive actuators applied to, for example, a measurement equipment, an optical modulator, an optical switch, an electric switch, a micro relay, a micro valve, a conveyance apparatus, an image display apparatus such as a display and a projector, an image drawing apparatus, a micro pump, a liquid drop discharge apparatus, a micro mixer, a micro stirrer, and a micro reactor. Likewise, a method for adjusting a piezoelectric/electrostrictive actuator of the present invention can suitably be used as a means for adjusting a displacement of various piezoelectric/electrostrictive actuators.

In addition, a method and an apparatus for testing a piezoelectric/electrostrictive sensor of the present invention can suitably be used as a means for testing various piezoelectric/electrostrictive sensors used for detecting fluid characteristics, sound pressure, micro weight, acceleration, or the like. A method for adjusting a piezoelectric/electrostrictive sensor of the present invention can suitably be used as a means for adjusting detection sensitivity of various piezoelectric/electrostrictive sensors.

The invention claimed is:

1. A method for testing a piezoelectric/electrostrictive actuator, the method including the steps of obtaining one or more frequency characteristic values of the piezoelectric/electrostrictive actuator selected from the group consisting of heights and areas of the peaks of resonance waveforms and a difference between a maximum and minimum value of a first order or first to higher orders of the resonance frequency characteristic values of the piezoelectric/electrostrictive actuator and the k-th order (k=1 to 4) of the first or first to higher orders of resonance frequencies; and
  estimating a displacement of the piezoelectric/electrostrictive actuator based on a relation between one or more of the obtained frequency characteristic values;
  wherein the piezoelectric/electrostrictive actuator comprises a support portion and a vibration portion, the vibration portion having a piezoelectric/electrostrictive actuating portion disposed thereon, and the piezoelectric/electrostrictive actuating portion comprising at least one piezoelectric/electrostrictive body sandwiched between at least two electrodes.

2. The method for testing a piezoelectric/electrostrictive actuator according to claim 1, wherein the relation is a relation of dividing the one or more frequency characteristic values selected from the group consisting of the heights and areas of the peaks of the resonance waveforms and the difference of the maximum and minimum of the first order of the resonance frequency characteristic values of the piezoelectric/electrostrictive actuator by the k-th order (k=1 to 4) of the first order of resonance frequency to estimate the displacement of the piezoelectric/electrostrictive actuator by the calculated value obtained by the division.

3. The method for testing a piezoelectric/electrostrictive actuator according to claim 1, wherein the relation is a relation of dividing a sum of the one or more frequency characteristic values selected from the group consisting of the heights and areas of the peaks of the resonance waveforms and the difference of the maximum and minimum of the first to higher orders of the resonance frequency characteristic values of the piezoelectric/electrostrictive actuator by the k-th order (k=1 to 4) of the first order of resonance frequency to estimate the displacement of the piezoelectric/electrostrictive actuator by the calculated value obtained by the division.

4. The method for testing a piezoelectric/electrostrictive actuator according to claim 1, wherein the relation is a relation of dividing the one or more frequency characteristic values selected from the group consisting of the heights and areas of the peaks of the resonance waveforms and the difference of the maximum and minimum of the resonance frequency characteristic value for each of the resonances of the first to higher orders of the piezoelectric/electrostrictive actuator by the k-th order (k=1 to 4) of resonance frequency and obtaining the sum of the values for each of the resonances to estimate the displacement of the piezoelectric/electrostrictive actuator by the calculated value obtained by the sum.

5. The method for testing a piezoelectric/electrostrictive actuator according to claim 2, wherein the displacement of the piezoelectric/electrostrictive actuator is estimated by a value obtained by further multiplying the calculated value by the capacitance of the piezoelectric/electrostrictive actuator.

6. A method for adjusting a piezoelectric/electrostrictive actuator comprising:
  estimating displacements of a plurality of piezoelectric/electrostrictive actuators according to the method for testing a piezoelectric/electrostrictive actuator of claim 1; and
  trimming the piezoelectric/electrostrictive body of the piezoelectric/electrostrictive portion of at least some of the plurality of piezoelectric/electrostrictive actuators to uniformly adjust the displacement of the piezoelectric/electrostrictive actuators uniformly.

7. The method for adjusting a piezoelectric/electrostrictive actuator according to claim 6, wherein both the piezoelectric/electrostrictive body and the upper electrode of at least some of the plurality of piezoelectric/electrostrictive actuators are trimmed.

* * * * *